(12) United States Patent
Zech et al.

(10) Patent No.: US 11,872,292 B2
(45) Date of Patent: Jan. 16, 2024

(54) CATIONICALLY AND RADIATION CURABLE COMPOSITION

(71) Applicant: 3M INNOVATIVE PROPERTIES COMPANY, St. Paul, MN (US)

(72) Inventors: Joachim W. Zech, Kaufering (DE); Hendrik Grupp, Ammersee (DE)

(73) Assignee: 3M Innovative Properties Company, St. Paul, MN (US)

( * ) Notice: Subject to any disclaimer, the term of this patent is extended or adjusted under 35 U.S.C. 154(b) by 1267 days.

(21) Appl. No.: 16/334,676

(22) PCT Filed: Sep. 12, 2017

(86) PCT No.: PCT/US2017/051057
§ 371 (c)(1),
(2) Date: Mar. 19, 2019

(87) PCT Pub. No.: WO2018/057335
PCT Pub. Date: Mar. 29, 2018

(65) Prior Publication Data
US 2019/0380917 A1 Dec. 19, 2019

(30) Foreign Application Priority Data
Sep. 22, 2016 (EP) .................................... 16190113

(51) Int. Cl.
| A61K 6/00 | (2020.01) |
| A61K 6/62 | (2020.01) |
| A61K 6/18 | (2020.01) |
| A61K 6/61 | (2020.01) |
| A61K 6/90 | (2020.01) |

(52) U.S. Cl.
CPC .................. *A61K 6/62* (2020.01); *A61K 6/18* (2020.01); *A61K 6/61* (2020.01); *A61K 6/90* (2020.01)

(58) Field of Classification Search
CPC ... A61K 6/62; A61K 6/61; A61K 6/18; A61K 6/90
See application file for complete search history.

(56) References Cited

U.S. PATENT DOCUMENTS

| 3,453,242 A | 7/1969 | Schmitt |
| 4,167,618 A | 9/1979 | Schmitt |
| 4,468,202 A | 8/1984 | Cohen |
| 4,657,959 A | 4/1987 | Bryan |
| 4,737,593 A | 4/1988 | Ellrich |
| 5,130,348 A | 7/1992 | Zahler |
| 5,249,862 A | 10/1993 | Herold |
| 5,286,105 A | 2/1994 | Herold |
| 5,426,134 A * | 6/1995 | Rheinberger .......... A61K 6/887 528/424 |
| 5,464,131 A | 11/1995 | Keller |
| 5,569,691 A | 10/1996 | Guggenberger |
| 5,750,589 A | 5/1998 | Zech |
| 5,918,772 A | 7/1999 | Keller |
| 6,395,801 B1 | 5/2002 | Bissinger |
| 6,653,375 B2 | 11/2003 | Moszner |
| 8,921,440 B2 * | 12/2014 | Weinmann ........... C08K 5/0025 520/1 |
| 2001/0004082 A1 | 6/2001 | Keller |
| 2003/0153726 A1 | 8/2003 | Eckhardt |
| 2004/0186195 A1* | 9/2004 | Suzuki .................. A61K 6/887 522/31 |
| 2006/0205838 A1 | 9/2006 | Velamakanni |
| 2007/0090079 A1 | 4/2007 | Keller |
| 2009/0042170 A1 | 2/2009 | Chen |
| 2013/0030076 A1* | 1/2013 | Weinmann ........... C08K 5/0025 522/31 |

FOREIGN PATENT DOCUMENTS

| AU | 68570/87 | 8/1987 |
| EP | 0231420 | 9/1991 |
| EP | 2022464 | 2/2009 |
| WO | WO 2005-016783 | 2/2005 |
| WO | WO 2007-047381 | 4/2007 |
| WO | WO 2007-104037 | 9/2007 |
| WO | WO 2009-061884 | 5/2009 |
| WO | WO 2009-151983 | 12/2009 |
| WO | WO 2010-147817 | 12/2010 |
| WO | WO 2011-133495 | 10/2011 |
| WO | WO 2012-177985 | 12/2012 |
| WO | WO 2015-006087 | 1/2015 |
| WO | WO 2016-196028 | 12/2016 |

OTHER PUBLICATIONS

International Search Report for PCT International Application No. PCT/US2017/051057, dated Dec. 5, 2017, 5 pages.

\* cited by examiner

*Primary Examiner* — Michael P Cohen

(57) ABSTRACT

The invention relates to a curable composition comprising a resin matrix, the resin matrix comprising cationically curable components (A) and radiation curable components (B), a curing system, the curing system comprising a starter (A-S) suitable for curing the cationically curable components (A) and a photo-initiator (B-I), the curable composition being provided as a Base Part and Catalyst Part being separated before use, wherein the Base Part comprises components (A) and (B) and wherein the Catalyst Part comprises components (A-S) and (B-I). The composition can be used for taking a dental impression including the subgingival parts.

19 Claims, 1 Drawing Sheet

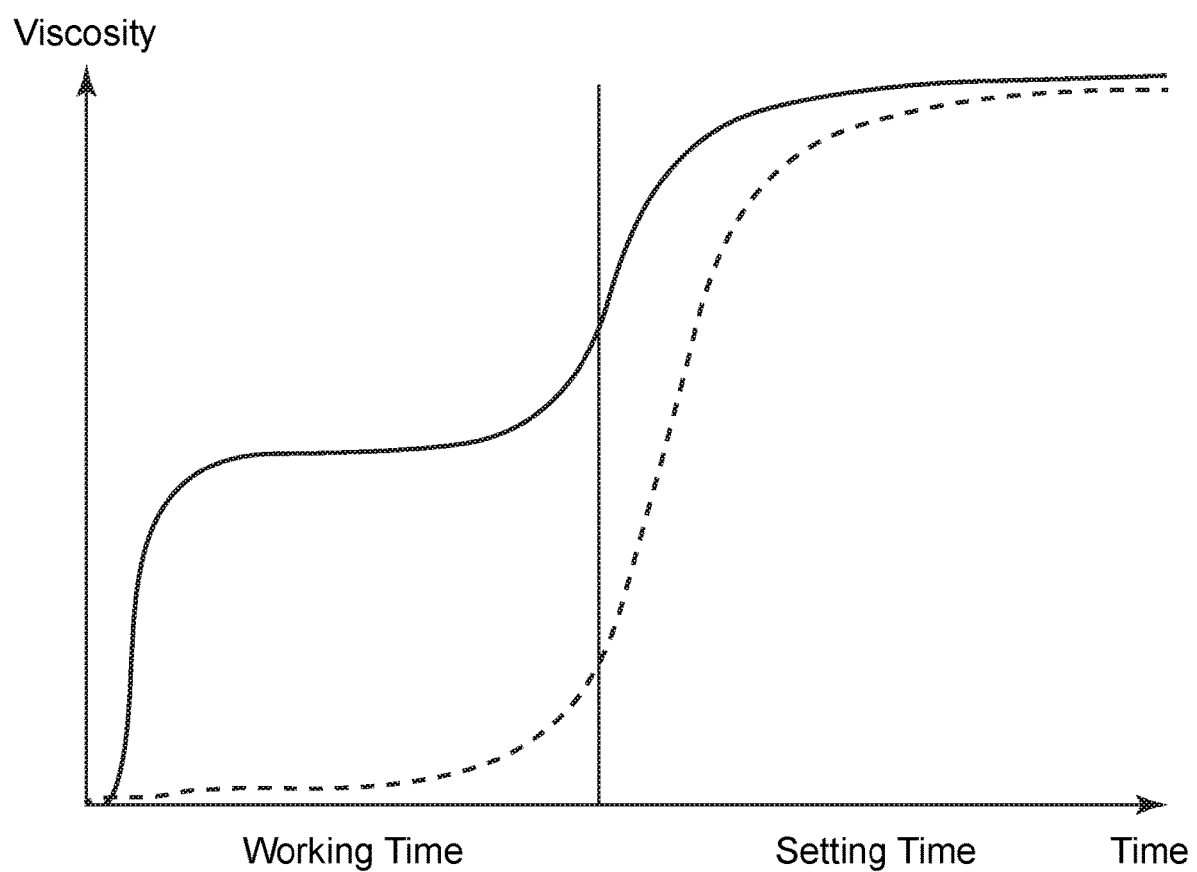

CATIONICALLY AND RADIATION CURABLE COMPOSITION

FIELD OF THE INVENTION

The invention relates to a curable composition comprising a resin matrix containing cationically curable components and radiation curable components. The curable composition further comprises a curing system with a starter suitable for curing the cationically curable components and a photo-initiator system. The curable composition is in particular useful in the dental field for taking dental impressions and conducting a dental retraction.

BACKGROUND ART

Prior to making a dental impression in most cases a so-called retraction must be done by which a small space is created between a tooth and the gingiva around the tooth. This is a prerequisite for a so called light-body impression material to flow into this small space so that a preparation margin which is subgingival can be captured with a high detail accuracy. Currently, different kinds of retraction processes and materials are known.

Many dentists still use dental retraction cords, which are placed in the sulcus of the tooth, remain there for a sufficient period of time and are removed later before conducting the impression process.

Alternatively, a dental retraction material can be used, which is inserted into the sulcus, kept there for a sufficient period of time and which is removed, as well, before the impression process is conducted.

In order to function as dental retraction material, the material has to have a certain stiffness or viscosity, which allows the retraction material to keep the sulcus open (withstand sulcus pressure).

A commercially available dental retraction material is e.g. provided by 3M Oral Care/3M ESPE under the brand 3M™ ESPE™ Retraction Capsule or 3M™ ESPE™ Astringent Retraction Paste, respectively.

In contrast to dental retraction materials, a dental impression material has to show good flowing properties and has typically a thin consistency.

Conducting such a separate retraction step is time consuming.
Patients and dentists nowadays have an increasing demand for a simplified method for taking dental impressions.

WO 2012/177985 A2 (Dentsply) relates to a tissue management impression material and a method of application into the sulcus of a patient, whereby the tissue management impression material is a part of the final dental impression made when manufacturing a dental device, such as a crown.

WO 2011/133495 A1 (3M) describes a radiation curable composition comprising (A) a cationically hardenable compound comprising at least one or two aziridine moieties having an aziridine equivalent weight in the range of about 250 to about 25,000 g/equivalent, and (B) a radiation sensitive starter, the radiation sensitive starter comprising a sulfonium salt comprising at least two aryl groups attached to the sulfonium ion, an iodonium salt, a ferrocenium salt, a combination or mixture thereof.

U.S. Pat. No. 4,468,202 (Cohen) relates to a method of obtaining a dental impression comprising the steps of: retracting the gingival tissue about the teeth of which a mold is to be obtained: applying a photocurable or chemical curable elastomeric material into the space between the teeth and the gingival tissue in close proximity to the teeth, the impression of which is desired: curing the elastomeric material to a degree such that it will retain the impression formed therein by the teeth; applying a second photocurable or chemical curable elastomeric material about the clinical crown of the teeth above and in contact with the subgingivally applied elastomeric material; curing the elastomeric material to a degree such that it will retain the impression formed therein by the teeth; and removing the cured elastomeric composite.

US 2009/042170 A1 (Chen at al.) describes a method for temporarily widening a gingival sulcus, the method comprising: inserting a composition within a gingival sulcus to be widened, and thereafter photo curing to polymerize the composition, the composition comprising a polymerizable monomer having at least one ethylenically unsaturated group, a photo polymerization initiator, and a fine inorganic powder, the method temporarily widening the gingival sulcus.

US 2004/0186195 A1 (Suzuki et al.) describes photopolymerization initiator comprising (A) a photo acid-generating compound such as a diaryliodonium salt, (B) a photo oxidation radical-generating compound, and (C) a fused polycyclic aromatic compound. The photopolymerization initiator makes it possible to polymerize cationically polymerizable monomers by the irradiation of visible light. For dental applications it is suggested to focus in particular on the use of oxetane and epoxy compounds.

None of the above described compositions and/or processes completely meets the practitioner's needs.

SUMMARY OF INVENTION

There is still a need for a composition and process which enables the practitioner to conduct the dental impression and dental retraction process more easily.

In particular it would be desirable if at least a part of the dental impression process and dental retraction process can be conducted with the same material.

Ideally a composition is desired, the viscosity of which can be adjusted on demand, i.e. a composition having a high viscosity desired for conducting a dental retraction step and a low viscosity desired for conducting a dental impressioning step.

This object can be achieved with the curable composition and the process described in the claims and the present text.

In one embodiment the present invention features a curable composition comprising
  a resin matrix, the resin matrix comprising
    cationically curable components (A) and
    radiation curable components (B),
  a curing system, the curing system comprising
    a starter (A-S) suitable for curing the cationically curable components (A) and
    a photo-initiator (B-I),
  the curable composition being provided as a Base Part and Catalyst Part being separated before use,
  wherein the Base Part comprises components (A) and (B) and
  wherein the Catalyst Part comprises components (A-S) and (B-I).

Such a curable composition can be used in a process for taking a dental impression including sub-gingival parts, the process comprising the steps of
  combining the Base Part and the Catalyst Part of the curable composition as described in any of claims 1 to 12 to obtain a curable composition, applying a portion X to the surface of dental tissue, in particular into the sulcus of a tooth, wherein radiation is applied to the portion X of the curable composition either during or at the end of the combining step, optionally applying radiation to the portion X of the curable composition after it has been applied to the dental tissue, applying a portion Y of the curable composition in contact with portion X of the curable composition to which radiation has been applied, optionally applying a dental impression material being different from the curable composition in contact with the curable composition, wherein the optionally applied dental impression material can also be applied to a partially hardened curable composition and letting the dental impression material harden, removing the composition and the optionally applied dental impression material from the dental tissue.

A further embodiment of the invention is directed to a kit of parts comprising the curable composition as described in the present text and at least one of a) a radiation source, b) a dental impression material as described in the present text.

The invention is also directed to a curing system comprising a starter suitable for curing cationically curable components as described in the present text, a photo-initiator comprising an alpha-diketon and/or phosphine oxide and optionally an amine accelerator and the use of such a curing system for curing the curable composition described in the present text.

A further embodiment of the invention is directed to a process of producing such a curable composition.

The invention is also directed to a process of curing the curable composition wherein the process comprises a mixing step and a step of applying radiation.

The invention is also directed to the cured composition obtained when curing the curable composition described in the present text.

BRIEF DESCRIPTION OF FIGURES

FIG. 1 exemplifies the change in viscosity of the composition described in the present text depending on the curing mode applied.

Unless defined differently, for this description the following terms shall have the given meaning:

The term "compound" or "component" is a chemical substance which has a particular molecular identity or is made of a mixture of such substances, e.g., polymeric substances.

By "paste" is meant a soft, viscous mass of solids dispersed in at least one liquid or a soft, viscous mass of a polymer.

A "particle" or "particulate filler" means a substance being a solid having a shape which can be geometrically determined. The shape can be regular or irregular. Particles can typically be analyzed with respect to e.g. grain size and grain size distribution. A particulate filler is composed of free-flowing particles. "Free-flowing" means that the particulate filler can be sieved, that is, it behaves like dry powdered sugar.

"Elastomeric" means rubber-elastic or rubber-like. Elastomeric materials can be characterized e.g. by a certain tensile strength and/or elongation at break. Other means for characterizing elastomeric materials include the measurement e.g. of the Young's modulus. Elastomeric materials typically have an E-modulus in the range from 0.8 to 10 MPa or from 1 to 8 MPa or from 1.5 to 6 MPa (determined e.g. according to DIN 53504, thickness of sample: 2 mm).

A "hardenable compound" is any compound which can be cured or solidified e.g. by chemical crosslinking. Chemical crosslinking can be initiated by using a redox or ionic initiator, radiation or heating thereby typically leading to a significant change in rheological properties like viscosity.

A "hardenable component or material" (e.g., "polymerizable component" or "crosslinkable component") is any component which can be cured or solidified e.g., by heating to cause polymerization, chemical crosslinking, radiation-induced polymerization or crosslinking by using a redox initiator. A hardenable component may contain, for example, only one, two, three or more polymerizable groups. Typical examples of polymerizable groups include unsaturated carbon groups, such as a vinyl group being present e.g. in a (meth)acrylate group.

A "resin matrix" shall mean the organic part of the dental composition being composed of the hardenable components and organic diluents, if present.

A "starter or initiator" is a substance or a group of substances being able to start or initiate or contribute to the hardening process of a hardenable compound.

"Radiation sensitive" means that the composition or a part of the composition is sensitive towards radiation and generates or helps to generate reactive species when exposed to the radiation. Those reactive species typically include radicals (charged or not charged), ions and mixtures thereof.

"Radiation curable" means that the composition can be cured or hardened using radiation alone or in combination with other initiators or starters, including redox initiators. The radiation typically comprises wavelength in the range from 250 to 1000 nm or from 350 nm to 700 nm.

The terms "vulcanizing", "hardening", "polymerizing", "crosslinking", "curing" and "setting" are used interchangeable and refer to compositions that have as a common attribute the development of a crosslinked polymer from relatively low molecular weight linear or branched polymers or pre-polymers by means of a chemical reaction that simultaneously forms these crosslinks and effectively extends chain length at room temperature.

"Poly" means that the respective substance contains at least 10 repeating units of a certain monomer moiety.

The term "crosslinked polymer" refers to polymers that are the result of the reaction of the functional group or groups of the polymer chains or prepolymers that were lengthened or connected, e.g., to form a crosslinked network. In contrast to a thermoplastic polymer (i.e., a polymer that softens and flows upon heating) a crosslinked polymer, after crosslinking, is characteristically incapable of further flow.

The term "cationically polymerizable compound" is defined as a compound which can be polymerised using an initiator containing or being able to generate cations, especially reactive cations.

A "prepolymer" is defined as a compound or a mixture of compounds obtainable by polymerization (such as e.g. polycondensation reaction) of monomers resulting in an intermediate product or mixture of products with increased molecular weight compared to the monomers used. The resulting intermediate product itself bears functional groups (either left over from the initial polymerization or introduced afterwards). The prepolymer containing functional groups can be used for further polymerization reactions (such as e.g. polycondensation reaction or polyaddition reaction) leading to a polymer or polymer mixture or a crosslinked polymer with increased molecular weight compared to the prepolymer.

"Aziridines" are a group of organic compounds sharing the aziridine functional group, which is a three membered heterocycle with one amine group and two methylene groups. The parent compound of the aziridines is called aziridine with molecular formula $C_2H_5N$.

An "alkyl-substituted aziridino group" is an aziridine group, wherein at least one of the hydrogen atoms of the methylene groups is substituted by an alkyl group, preferably by a C1 to C4 alkyl group, e.g. methyl, ethyl, n- and iso-propyl or n-, iso- or tert.-butyl group. In the chemical literature a "methyl substituted aziridine" is sometimes also referred to as "propylene imine".

"Polyether" or "polyether group containing compound" are compounds having a molecular weight of at least 150 g/mol and containing in the backbone at least 3, 10 or 20 ether moieties. Polyether containing compositions used as dental impression material can be cured by different mechanisms. Widely used is a crosslinking reaction using aziridine groups.

Examples of polyether and aziridino groups containing impression materials are given in U.S. Pat. No. 5,569,691 (Guggenberger et al.), and U.S. Pat. No. 5,130,348 (Zahler et al.). Commercially available materials are sold e.g. under the brand Impregum™ (3M ESPE).

A "monomer" is any chemical substance which can be characterized by a chemical formula, bearing one or more polymerizable groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth)acryloxy" group is a shorthand term referring to either an acryloxy group (i. e., $CH_2=CH-C(O)-O-$) and/or a methacryloxy group (i. e., $CH_2=C(CH_3)-C(O)-O-$). Similarly, (meth)acrylate is a shorthand term referring to "acrylate" and/or "methacrylate."

By "derivative" is meant a chemical compound showing a chemical structure closely related to the corresponding reference compound and containing all featured structural elements of the corresponding reference compound but having small modifications like bearing in addition comparably small additional chemical groups like e.g. $CH_3$, Br, Cl, or F or not bearing comparably small chemical groups like e.g. $CH_3$ in comparison to the corresponding reference compound. A derivative of a certain compound comprises the chemical structure of that compound, but may contain other side groups or moieties.

The following examples might illustrate this: tetramethyl bis-phenol A bearing four additional methyl groups with respect to the reference compound bis-phenol A, and bis-phenol F not bearing two additional methyl groups with respect to the reference compound bis-phenol A are derivatives of bis-phenol A within the meaning of this definition.

"Room temperature curable" implies that the curing reaction can proceed at temperatures at or near 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is retarded) at room temperature for prolonged periods. The compositions of the invention are room temperature vulcanizing.

A "dental composition" or a "composition for dental use" or a "composition to be used in the dental field" is any composition which can be used in the dental field. In this respect the composition should not be detrimental to the patients' health and thus free of hazardous and toxic components being able to migrate out of the composition.

Examples of dental compositions include permanent and temporary crown and bridge materials, artificial crowns, anterior or posterior filling materials, adhesives, mill blanks, lab materials and orthodontic devices.

Dental compositions are typically hardenable compositions, which can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health.

Dental compositions are typically provided to the practitioner in comparable small volumes, that is volumes in the range from about 0.1 to about 500 ml or from about 0.5 to about 100 ml or from about 1 to about 50 ml. Thus, the storage volume of useful packaging devices is within these ranges.

A "dental impression" may be described as an accurate representation of part or all of a person's dentition. It forms a "negative" of a person's hard dental tissue which can then be used to make a model (physical) of the dentition. This may be used for the fabrication of dentures, crowns or other prostheses. An impression is typically carried out by placing a viscous material into the mouth in a customised or stock tray. The material then sets to become an elastic solid, and when removed from the mouth retains the shape of the teeth and gingiva.

A "dental impression material" is a material used for making impressions of the tooth structure. A dental impression material is usually applied on a dental impression tray. A dental impression material can be based on different chemical substances and crosslink by various chemical reactions. Common materials used for dental impressions include alginate, agar, polyethers including aziridine substituted polyether materials as well as silicones, both condensation-cured silicones and addition-cured silicones including polyvinyl siloxanes (so-called VPS materials).

The term "dental impression materials" comprises precision impression materials, situation impression materials, bite registration materials, duplicating materials (applicable for the duplication of master models, e.g. for all-ceramic restorations requiring a refractory investment model and when inlays, onlays, cantilevers and other precision attachments are being fabricated) and modelling materials (applicable for e.g. reconstructing the gingival, producing crowns and bridges). Duplicating and modelling materials are commercially available e.g. from 3M ESPE under the trademarks or Vestogum™.

A "putty like dental impression material" is a kneadable dental impression material having a consistency of 35 mm or below according to ISO 4823:2015-08.

A "dental retraction material" is a material intended to be placed in the gingival sulcus, that is, the natural space between the hard dental tissue (i.e. tooth structure) and the gum tissue that surrounds the hard dental tissue. Once placed in the gingival sulcus, the dental retraction material will exert pressure on the surrounding tissue resulting in a widening of the gingival sulcus to enable the practitioner to get a more precise impression of the dental situation below the gum line during a dental impression process. Like a dental impression material, a dental retraction material is removed from the mouth of the patient after use.

The term "automixer-suitable material" relates to a multi-component material which can be dispensed, for example, from a two-component disposable cartridge through a static mixer, e.g., of SulzerMixpac Company (U.S. Pat. No. 5,464,131, US 2001/0004082) or from tubular film bags in dual-chamber reusable cartridges through a dynamic mixer, e.g., in the "Pentamix™", "Pentamix™ 2" and "Pentamix™ 3" devices of 3M ESPE Company (cf. U.S. Pat. Nos. 5,286,105 and 5,249,862).

The term "dental tissue" includes the hard tooth substance (enamel and dentin), the gingival region (soft dental tissue) surrounding the hard tooth substance and hard tooth substance bearing orthodontic appliances.

A "temporary crown and bridge material" within the meaning of the invention is a hardenable material used for making dental crowns and bridges. These materials are typically used during the time period a dental technician needs for producing a permanent prosthetic work such as a crown or bridge. These time periods can last from a few days (1 to 6 days), a few weeks (1 to 4 weeks) or a few months (1 to 6 month).

A "surfactant" is an agent imparting wettability to a material, that is making the material more wettable compared to a material not containing a surfactant. The wettability can be determined by the water contact angle which can be measured using e.g. a goniometer DSA 10 (Krüss). A low water contact angle indicates a better wettability.

"Molecular weight" in the context of the invention and if not otherwise indicated always means number average molecular weight ($M_n$). The molecular weight (Mn) of the polymerizable compound before setting can be determined using nuclear magnetic resonance spectroscopy (end-group determination). In this respect proton ($^1H$) NMR techniques are employed to estimate the molecular weight of the precursor of the prepolymer. Integrated signals of the terminal —$CH_2$— groups are compared to the integrated sum of proton signals from backbone hydrocarbon protons taking into account co-monomer ratio, if applicable. To achieve appropriate separation of terminal methylene proton signals from the backbone proton signals, terminal hydroxyl groups are esterified with trifluoroacetic acid.

"Ambient conditions" within the meaning of the invention mean the conditions which the inventive solution is usually subjected to during storage and handling. Ambient conditions may for example: be a pressure of 900 to 1100 mbar, a temperature of −10 to 60° C. and a relative humidity of 10 to 100%. In the laboratory ambient conditions are adjusted to 23° C. and 1013 mbar.

A composition or solution is "essentially or substantially free of" a certain component within the meaning of the invention, if the composition or solution does not contain said component as an essential feature. Thus, said component is not wilfully added to the composition or solution either as such or in combination with other components or ingredient of other components. A composition being essentially free of a certain component usually contains the component in an amount of less than 1 wt. % or less than 0.1 wt. % or less than 0.01 wt. % with respect to the whole composition. Ideally the composition does not contain the said component at all. However, sometimes the presence of a small amount of the said component is not avoidable e.g. due to impurities.

As used herein, "a", "an", "the", "at least one" and "one or more" are used interchangeably. The terms "comprises" or "contains" and variations thereof do not have a limiting meaning where these terms appear in the description and claims.

Also herein, the recitations of numerical ranges by endpoints include all numbers subsumed within that range (e.g., 1 to 5 includes 1, 1.5, 2, 2.75, 3, 3.80, 4.5, etc.).

"Comprise" includes the terms "contain", "essentially consists of" and "consists of".

Adding an "(s)" to a term means that the term should include the singular and plural form. E.g. the term "additive(s)" means one additive and more additives (e.g. 2, 3, 4, etc.). Unless otherwise indicated, all numbers expressing quantities of ingredients, measurement of properties used in the specification and claims are to be understood as being modified in all instances by the term "about". Any numerical value, however, inherently may contain certain errors necessarily resulting from the standard deviations found in their respective testing measurements.

Unless described otherwise, "wt. %" refers to the weight of the composition obtained when combining the compositions of Part A and Part B of the kit of parts, which is also referred to as "whole composition". Further, all references cited within the present text are herewith incorporated by reference.

DETAILED DESCRIPTION

Cationically curing dental impression materials like those comprising a polyether backbone and pending aziridino moieties are typically cured by using Lewis- or Broensted acids like e.g. sulfonium salts.

The curing reaction can be split into a working time period and a setting time period.

During the working time period of such a material, the viscosity of the composition is still low, increases only slowly and thus allows an adjustment of the composition in the mouth of a patient by the practitioner.

After a certain period of time, the viscosity increases more rapidly during which the curing is completed. This period is called setting time.

It was found that by addition of radiation curable components in combination with a photo-initiator, the curing behavior of the curable composition can be influenced by application of radiation with the benefit that the consistency of the composition can be rapidly increased on demand.

In this respect the curable composition described in the present text comprises two different curing mechanisms, a chemically curing mechanism typically induced by Lewis and/or Broensted acids or the respective precursors thereof and a radiation induced curing mechanism, typically based on the combination of an alpha-diketon component and an accelerator such as an amine.

Radiation curable components comprising (meth)acrylate moieties, preferably in combination with urethane moieties were found to be particularly useful.

A curable composition, the curing behavior of which can be triggered according to the practitioner's needs by applying radiation is beneficial for a so-called retraction impressioning process. Such a process enables the practitioner to conduct a retraction step and an impressioning step in a patient's mouth by using only one material.

In contrast to the invention, the processes suggested in the prior art such as described in WO 2012/177985 A2 (Dentsply) or U.S. Pat. No. 4,468,202 (Cohen) require the application of two different materials.

Further, contrary to expectation on the surface of the cured composition no smear layer or oxygen inhibition layer was found.

The occurrence of smear layers is well known with respect to dental composite filling material or temporary crown and bridge materials, the curing of which is typically based on the radiation curing of (meth)acrylates as well. If brought in contact with air, the surface of such materials often forms a sticky layer called oxygen inhibition layer.

Such a layer is typically not desired as it can prevent good connection or adhesion to further or different materials which may be applied later to the cured composition In contrast to these (meth)acrylate containing materials of the art, the curable composition described in the present text surprisingly cures without the formation of a smear layer.

The reason for this effect is unknown. But it seems that the combination of (meth)acrylates with cationically curing components plays a role.

The curable composition described in the present text is typically processed or used as follows:

In a first step a first portion of the compositions of the Base Part and Catalyst Part is mixed e.g. by a static mixing tip. The composition is in a low viscous and flowable stage. During or after mixing radiation is applied to the first portion. The application of radiation causes an increase of viscosity and/or consistency of the first portion of the curable composition.

In a second step the first portion of the composition is applied into the sulcus of a tooth of a patient. If desired, the application of radiation can be continued.

Alternatively, the application of radiation is done during the application of the first portion of the composition into the sulcus.

After the first portion of the composition has been placed in the sulcus of a patient, the radiation exposure to the composition is typically stopped.

The curing of the partially cured first portion of the composition continues. At this stage of the process, the curing is caused by the starter component for the cationically curable components being present in the curable composition.

A low viscous composition which has not been exposed to radiation and which has not been applied into the sulcus remains. If desired, this part of the composition can be used as dental impression material (so-called "wash material").

In a third step a second portion of the remaining composition is applied in contact with, preferably on top of the first portion of the composition.

If desired, radiation can also be applied to the second portion of the composition.

After final curing, the first portion and the second portion of the composition are removed from the mouth of the patient.

This is typically done by using a dental impression material (so-called "tray material"). The dental impression material can be either a material being different from the curable composition described in the present text or it can be the same material.

In another embodiment the tray material can be applied to the first and second portion of the composition while at least the second portion is not fully cured yet. That is, the composition of the second portion has still a flowable consistency. A composition having a flowable consistency is typically within its working time. The working time is typically determined by the cationic curing mechanism.

Thus, the curable composition described in the present text enables the practitioner to easily switch between a high viscosity and a low viscosity mode. This switch can be done on demand in the course of a dental impressioning procedure. The switch can be achieved by simply exposing the curable composition to radiation.

In this case the radiation curable components start cross-linking within the mixed paste leading to a rapid increase of viscosity. This is the so-called retraction-mode of the material.

If the mixed material is not exposed to light, the viscosity of the mixed paste remains thin because the radiation curable components do not react and so this material can be used to make a regular impression of the rest of the tooth. This is the so-called impressioning-mode of the material. In this mode curing of the curable composition is effected by the cationically induced mechanism only.

The curing mechanism induced by radiation is typically faster than the curing mechanism induced by reaction of the starter component with the cationically curable components.

In FIG. 1 the curing behaviour of the curable composition described in the present text is schematically exemplified.

On the x-axis of FIG. 1 the time is given, on the y-axis the viscosity. The time is split into two sections: working time and setting time.

The lower curve (dashed line) shows the curing behaviour of the curable composition after mixing the Base Part and the Catalyst Part without application of radiation. At the end the composition is in a cured or set rubber stage.

The curing behaviour is triggered by the starter (A-S) suitable for curing the cationically curable components (A) only. This curing behaviour is referred to as "Impression Mode".

The upper curve (solid line) shows the curing behaviour of the curable composition after mixing the Base Part and the Catalyst Part and application of radiation.

The curing behaviour is now triggered by the two separate curing systems present in the curable composition. The two curing systems run in parallel.

However, the radiation induced curing of the radiation curable components (B) is faster than the curing based on the curing of the cationically curable components (A).

As a result, a rapid increase of viscosity to a first level of the composition is observed. This curing behaviour is referred to as "Retraction Mode".

The final curing to the second level is affected by the curing of the cationically curable components (A).

Thus, compared to the "Impression Mode" having only one final curing level, the curable composition processed in the "Retraction Mode" shows a step-wise curing.

A light-curable polyether based dental impression material is already described in WO 2011/133495 A1 (3M). However, the curing of the curable composition described in WO 2011/133495 A1 is essentially based on the cationically curing of cationically curable components. A composition comprising a two-component curing system in combination with cationically curable components and radiation curable components as suggested in the present text is not described.

The curable composition described in the present text can typically be characterized by one or more of the following properties:

Viscosity of Base Part and/or Catalyst Part before curing: from 2 to 500 Pa*s or from 30 to 150 Pa*s at 23° C.;

Consistency: less than 45 mm, after exposure to light and if determined according to ISO 4823:2015-08;

Shore hardness A: from 35 to 90, after exposure to light and if determined according to DIN 53505:2000-8 24 h after mixing the Base Part and the Catalyst Part;

Hardening within 15 min within a temperature range from 20 to 40° C. to a rubber elastic mass after mixing the Base Part and the Catalyst Part.

If desired, the respective properties can be determined as described in the example section.

The curable composition described in the present text comprises a resin matrix and a curing system.

The resin matrix comprises cationically curable components and radiation curable components.

The ratio of cationically curable components to radiation curable components is typically from 20:1 to 1:2 or from 10:1 to 1:1 with respect to weight.

Using such a ratio can be beneficial as it allows a good balance between the properties of the composition in the retraction mode and the composition in the impression mode.

If the radiation curable components are used in excess compared to the cationically curable components, the radiation cured composition may become too hard. This may negatively affect the elastomeric properties required for a dental impression material.

The nature and structure of the cationically curable component (A) is not particularly limited unless the desired result cannot be achieved.

The cationically curable component according to component (A) typically comprises a backbone and at least one or two reactive functional group(s).

The backbone of the cationically curable component typically comprises moieties selected from polyether, polyester, polyurethane, silicone, polyalkylene, polystyrol, polysulfide and combinations thereof.

In the dental field a polyether moieties containing backbone can be preferred. Those groups typically also improve the hydrophilic properties of the composition.

According to one embodiment, the cationically curable component includes a polyether group containing hardenable prepolymer as component (A) or part of component (A), that is, a prepolymer comprising a polyether group(s) and reactive moieties which upon addition of a suitable catalyst or initiator can react with each other and thus form a polymeric network.

The molecular weight (Mn) of the polyether group(s) containing prepolymer is typically in a range from 150 to 20,000 g/mol, or in the range from 250 to 10,000 g/mol, determined e.g. with GPC methods know to the person skilled in the art.

Suitable polyethers or polyether groups, which can be used, include those which meet the requirements in terms of material properties with regard to the preferred use as dental materials.

Appropriate polyethers or polyether groups can be produced in a manner known to the person skilled in the art by the reaction of the starting compound having a reactive hydrogen atom with alkylene oxides, for example ethylene oxide, propylene oxide, butylene oxide, styrene oxide, tetrahydrofurane or epichlorohydrine or mixtures of two or more thereof.

Especially suitable are polyether compounds which are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

The reaction products of low-molecular-weight polyfunctional alcohols having at least two hydroxyl groups with alkylene oxides, so-called polyethers, may also be used as polyols. The alkylene oxides preferably have from 2 to 4 carbon atoms. Suitable polyols are, for example, the reaction products of ethylene glycol, propylene glycol, butanediol or hexanediol isomers with one or more of the following alkylene oxides: ethylene oxide, propylene oxide or butylene oxides like tetrahydrofurane. Furthermore, the reaction products of polyfunctional alcohols such as glycerol, trimethylolethane or trimethylolpropane, pentaerythritol or sugar alcohols, or mixtures of two or more thereof, with the mentioned alkylene oxides, forming polyether polyols are also suitable.

Suitable starting compounds are, for example, water, ethylene glycol, 1,2- or 1,3-propylene glycol, 1,4- or 1,3-butylene glycol, 1,6-hexanediol, 1,8-octanediol, neopentyl glycol, 1,4-hydroxymethylcyclohexane, 2-methyl-1,3-propanediol, glycerol, trimethylolpropane, 1,2,6-hexanetriol, 1,2,4-butanetriol, trimethylolethane, pentaerythritol, mannitol, sorbitol, or mixtures of two or more thereof.

Especially suitable are polyether compounds as are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

For example, polyether polyols which are prepared by copolymerisation of tetrahydrofuran and ethylene oxide in a molar ratio of from 10:1 to 1:1, preferably to 4:1, in the presence of strong acids, for example boron fluoride etherates, are suitable.

The composition comprises at least a cationically curable component having at least 1 aziridine moiety or more, if desired, e.g. at least 2 or 3 or 4 or 5 or 6 aziridine moieties. Using a cationically curable component with at least 2 azirdine moieties can be preferred to ensure a sufficient crosslinking.

According to another embodiment, the cationically curable component comprises on average at least 2 aziridine moieties.

The term "on average" is to be interpreted such in the context of the present text that a mixture of a large number of compounds may comprise both compounds having less than 2 aziridino groups and also compounds having more than 2 aziridine groups although, when seen over the entirety of the compounds of component (A), the average functionality of all molecules is, with respect to aziridine groups, 2 or more.

All mentioned types of polyaddition or polycondensation products can be provided with aziridine groups by means of any desired subsequent reactions known to the person skilled in the art. For example, it is possible first to introduce, into an appropriate polymer, substituents which are in turn capable of reacting with suitable aziridine derivatives.

It is also possible to polymerise cyclic ethers, preferably epoxides, onto the chain so that products are obtained which at the end contain substituents which can react with aziridine. There come into consideration, for example, polyethers onto which halo-substituted epoxides, e.g. epibromohydrin, are polymerised.

Suitable possible methods for providing the polymers with aziridine groups are mentioned, e.g., in U.S. Pat. No. 3,453,242 (Schmitt et al.).

Suitable polymers carry the aziridine groups terminally or laterally, or terminally and laterally, but preferably terminally.

The aziridine groups containing compound typically have a dynamic viscosity $\eta$ of from 10 to 500 Pa*s, especially from 15 to 300 Pa*s. A preferred viscosity range is from 20 to 180 Pa*s at 23° C.

The aziridine equivalent is typically from 250 to 25,000 g/equivalent, especially from 400 to 10,000 g/equivalent.

The term "aziridine equivalent" is defined as (molecular mass of the molecule)/(number of aziridine groups present in the molecule).

Using compounds having such an aziridine equivalent weight may facilitate the provision of rubber-like or elastomeric materials (after hardening). Compounds having an aziridine equivalent weight outside this range might either be too hard or brittle or too soft, e.g. do not have the desired Shore hardness or tensile strength.

The cationically curable component which can be used may comprise only one type of aziridine group containing polymer. It is, however likewise possible for the cationically hardenable compound to comprise two or more different types of aziridine polymers, for example 3, 4 or 5 different types.

A "type of polymer" is understood, in the context of the present invention, to be a polymer as results from the polyaddition or polycondensation of selected monomers under the selected reaction conditions. A type of polymer can accordingly include polymer molecules of differing chemical constitution and differing molecular weight, depending on the reaction conditions selected. However, two reactions carried out using identical monomer compositions under identical reaction conditions always result, in accordance with the invention, in identical types of polymer. Two reactions which are carried out using identical monomers but under different reaction conditions may result in identical types of polymers but need not do so. The crucial factor therein is whether there are identifiable differences—in terms of chemical constitution, molecular weight and further parameters which can be determined—that are of relevance to the material properties. Two reactions which are carried out using different monomer compositions always result, in accordance with the invention, in different types of polymers.

Reactive side groups which pending from or attached to the backbone of the prepolymer include those characterized by the following formula

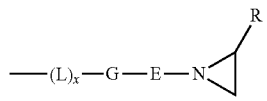

wherein R represents H, $C_1$-$C_{12}$ alkyl, $C_2$-$C_{12}$ alkenyl, $C_2$-$C_{12}$ alkinyl, $C_7$-$C_{15}$ alkylaryl, $C_7$-$C_{15}$ arylalkyl, $C_3$-$C_{12}$ cycloalkyl, and wherein hydrogen atoms may be replaced by Cl or F and/or wherein up to five carbon atoms may be replaced by atoms or group of atoms selected from O, CO, N, S, E represents a $C_1$-$C_{18}$ branched or unbranched hydrocarbon chain wherein up to five carbon atoms may be replaced by atoms or group of atoms selected from O, CO, N, S, G represents a group selected from C(O)O, C(O)NR, C(O), C(O)C(O), C(O)(CH$_2$)$_m$C(O) with m=1 to 10, C(S)NR, CH$_2$, L represents O, S, NR with x=0 or 1.

It can be preferred, if the cationically curable component has a linear molecular structure. Thus, the cationically curable component may typically comprise a linear backbone, which is typically end-capped with aziridine groups. Usually, there are no side chains, especially cationically hardenable side chains pending from the backbone.

The cationically curable component is typically present in an amount, which allows the formation of a sufficiently crosslinked network, in order to fulfil the practitioners needs.

By varying the amount of the cationically curable component, e.g. the viscosity and the hardness of the cured composition can be adjusted.

If the amount of the cationically curable component is too low, the resulting composition might not cure within the desirable period of time or might show not desirable mechanical properties.

If the amount of the cationically curable component is too high, the resulting composition might be too viscous.

If desired, besides the cationically curable component containing at least two aziridine groups, further curable compounds can be present being different from the cationically hardenable compound described above.

Thus, blends of various cationically polymerizable resins are also contemplated in the present text. Examples of such blends include two or more weight average molecular weight distributions of resin-containing compounds, such as low molecular weight (below 200), intermediate molecular weight (200 to 10,000) and higher molecular weight (above 10,000).

Alternatively or additionally, the resin may contain a blend of resin-containing materials having different chemical natures, such as aliphatic and aromatic, or functionalities, such as polar and non-polar. Other cationically polymerizable polymers may additionally be incorporated, if desired.

The cationically curable component (A) is typically present in the following amounts:
Lower amount: at least 5 or 12 or 15 wt. %;
Upper amount: at most 90 or 85 or 78 wt. %;
Range: from 5 to 90 or from 12 to 85 or from 15 to 78 wt. %, wt. % with respect to the weight of the whole composition.

The radiation curable components (B) can typically be characterized by one or more of the following properties:
being radiation curable at a wave length in the range from 380 to 800 nm;
viscosity: from 0.01 to 100 Pa*s or from 0.1 to 20 Pa*s at 23° C.;
molecular weight: from 200 to 3,000 g/mol, or from 400 to 2,700 or from 1,000 to 2.500 g/mol.

Molecules having a molecular weight above about 200 g/mol or above about 400 g/mol are usually less volatile than molecules having a lower molecular weight and thus may contribute to providing a biocompatible composition.

Using a viscosity in the above mentioned range may facilitate the manufacturing process of the curable composition to obtain a homogeneous composition.

The radiation curable component (B) typically comprises at least one or more (e.g. two to four) (meth)acrylate moieties.

Besides a (meth)acrylate moiety, the radiation curable component (B) may also comprise one or more urethane moieties.

According to a preferred embodiment, the radiation curable component (B) comprises at least two (meth)acrylate moieties and at least one urethane moiety.

Thus, the radiation curable component (B) can be characterized as a urethane (meth)acrylate.

The radiation curable component (B) does typically not comprise an acidic moiety. An acidic moiety may negatively interfere with the cationically curable moieties of component (A).

Examples for radiation curable component (B) comprising at least two (meth)acrylate moieties include ethylene glycol di(meth)acrylate, diethylene glycol di(meth)acrylate, triethylene glycol di(meth)acrylate, tetraethylene glycol di(meth)acrylate, polyethylene glycol di(meth)acrylate, 1,3- butylene glycol di(meth)acrylate, 1,6-hexane diol di(meth) acrylate, neopentyl glycol di(meth) acrylate, tripropylene glycol di(meth) acrylate, polypropylene glycol di(meth) acrylate, glycerol di(meth)acrylate, bisphenol A di(meth) acrylate, bisphenol A glycidyl di(meth)acrylate, bisphenol A propyl di(meth)acrylate, bisphenol A isopropyl di(meth) acrylate, ethylene oxide modified bisphenol A di(meth) acrylate, ethylene oxide modified bisphenol A glycidyl di(meth)acrylate, 2,2-bis(4-methacryloxypropoxyphenyl) propane, 7,7,9-trimethyl-4,13-dioxy-3,14-dioxa-5,12-diazahexadecane-1,16-diol di(meth)acrylate, neopentyl glycol hydroxypivalic acid ester di(meth)acrylate, caprolactone modified hydroxypivalic acid neopentyl glycol ester di(meth)acrylate, trimethylol ethane di(meth)acrylate, trimethylol propane di(meth)acrylate, trimethylol methane tri(meth) acrylate, trimethylol ethane tri(meth)acrylate, trimethylol propane tri(meth)acrylate, pentaerythritol tri(meth)acrylate, dipentaerythritol tri(meth)acrylate, pentaerythritol tetra(meth)acrylate, dipentaerythritol tetra(meth)acrylate, dipentaerythritol hexa(meth)acrylate, the reaction product of 3-chloro-2-hydroxypropyl (meth)acrylate and methylcyclohexane diisocyanate, the reaction product of 2-hydroxypropyl (meth)acrylate and methylcyclohexane diisocyanate, the reaction product of 2-hydroxypropyl (meth)acrylate and methylene bis (4-cyclohexylisocyanate), the reaction product of 2-hydroxypropyl(meth)acrylate and trimethylhexamethylene diisocyanate, the reaction product of 2-hydroxyethyl (meth)acrylate and isophorone diisocyanate, and the reaction product of 3-chloro-2-hydroxypropyl (meth)acrylate and isophorone diisocyanate, methyl (meth)acrylate, ethyl (meth)acrylate, propyl methacrylate, isopropyl methacrylate, n-butyl (meth)acrylate, iso-butyl (meth)acrylate, 2-ethylhexyl (meth)acrylate, lauryl (meth)acrylate, tridecyl (meth)acrylate, stearyl (meth)acrylate, cyclohexyl (meth) acrylate, benzyl (meth)acrylate, 2-hydroxyethyl (meth)acrylate, 2-hydroxypropyl (meth)acrylate, glycidyl (meth)acrylate, tetrahydrofurfuryl (meth)acrylate, allyl (meth)acrylate, 2-ethoxyethyl (meth)acrylate, methoxydiethylene glycol (meth)acrylate, methoxytetraethylene glycol (meth)acrylate, methoxypolyethylene glycol (meth)acrylate, phenoxy-diethyleneglycol (meth)acrylate, phenoxyhexaethyleneglycol (meth)acrylate, glycerol (meth)acrylate, tetrahydrofurfuryl (meth)acrylate, dicyclopentenyl (meth)acrylate, isobornyl (meth)acrylate, phenyl (meth)acrylate, pentaerythritol mono (meth)acrylate, dipentaerythritol mono(meth)acrylate, and mixtures thereof.

According to one embodiment the curable composition comprises at least one urethane(meth)acrylate with at least two (meth)acrylate moieties.

If desired, the curable composition may comprise at least two, three or four different kinds of radiation curable components (B). Using an urethane(meth)acrylate is sometimes preferred.

Compared to (meth)acrylates without an urethane moiety, urethane(meth)acrylate showed even an improved viscosity enhancing effect upon radiation.

The urethane (meth)acrylates employed in the composition described in the present text are typically obtained by reacting an NCO-terminated compound with a suitable monofunctional (meth)acrylate monomer such as hydroxyethyl acrylate, hydroxyethyl methacrylate, hydroxypropylmethacrylate, preferably hydroxyethyl- and hydroxypropylmethacrylate.

Urethane (meth)acrylates may be obtained by a number of processes known to the skilled person. For example, a polyisocyanate and a polyol may be reacted to form an isocyanate-terminated urethane prepolymer that is subsequently reacted with a (meth)acrylate such as 2-hydroxy ethyl(meth)acrylate. These types of reactions may be conducted at room temperature or higher temperature, optionally in the presence of catalysts such as tin catalysts, tertiary amines and the like.

Polyisocyanates which can be employed to form isocyanate-functional urethane prepolymers can be any organic isocyanate having at least two free isocyanate groups. Included are aliphatic cycloaliphatic, aromatic and araliphatic isocyanates.

Any of the known polyisocyanates such as alkyl and alkylene polyisocyanates, cycloalkyl and cycloalkylene polyisocyanates, and combinations such as alkylene and cycloalkylene polyisocyanates can be employed.

Preferably, diisocyanates having the formula $X(NCO)_2$ are used, with X representing an aliphatic hydrocarbon radical with 2 to 12 C atoms, a cycloaliphatic hydrocarbon radical with 5 to 18 C atoms, an aromatic hydrocarbon radical with 6 to 16 C atoms and/or an araliphatic hydrocarbon radical with 7 to 15 C atoms.

Examples of suitable polyisocyanates include 2,2,4-trimethylhexamethylene-1,6-diisocyanate, hexamethylene-1,6-diisocyanate (HDI), cyclohexyl-1,4-diisocyanate, 4,4'methylene-bis(cyclohexyl isocyanate), 1,1'-methylenebis(4-isocyanato) cyclohexane, isophorone diisocyanate, 4,4'-methylene diphenyl diisocyanate, 1,4-tetramethylene diisocycanate, meta- and para-tetramethylxylene diisocycanate, 1,4-phenylene diisocycanate, 2,6- and 2,4-toluene diisocycanate, 1,5-naphthylene diisocycanate, 2,4' and 4,4'-diphenylmethane diisocycanate and mixtures thereof.

It is also possible to use higher-functional polyisocyanates known from polyurethane chemistry or else modified polyisocyanates, for example containing carbodiimide groups, allophanate groups, isocyanurate groups and/or biuret groups. Particularly preferred isocyanates are isophorone diisocyanate, 2,4,4-trimethyl-hexamethylene diisocyanate and higher-functional polyisocyanates with isocyanurate structure.

The isocyanate terminated urethane compound is capped with a (meth)acrylate to produce a urethane (meth)acrylate compound. In general, any (meth)acrylate-type capping agent having a terminal hydroxyl group and also having an acrylic or methacrylic moiety can be employed, with the methacrylic moiety being preferred.

Examples of suitable capping agents include 2-hydroxyethyl(meth)acrylate, 2-hydroxypropyl (meth)acrylate, glycerol di(meth)acrylate and/or trimethylolpropane di(meth) acrylate. Particularly preferred are 2-hydroxyethyl methacrylate (HEMA) and/or 2-hydroxyethyl acrylate (HEA).

The equivalence ratio of isocyanate groups to compounds reactive vis-à-vis isocyanate groups is 1.1:1 to 8:1, preferably 1.5:1 to 4:1.

The isocyanate polyaddition reaction can take place in the presence of catalysts known from polyurethane chemistry, for example organotin compounds such as dibutyltin dilaurate or amine catalysts such as diazabicyclo[2.2.2]octane. Furthermore, the synthesis can take place both in the melt or in a suitable solvent which can be added before or during the prepolymer preparation. Suitable solvents are for example acetone, 2-butanone, tetrahydrofurane, dioxane, dimethylformamide, N-methyl-2-pyrrolidone (NMP), ethyl acetate, alkyl ethers of ethylene and propylene glycol and aromatic hydrocarbons. The use of ethyl acetate as solvent is particularly preferred.

Suitable examples of urethane (meth)acrylates include 7,7,9-trimethyl-4,13-dioxo-3,14-dioxa-5,12-diazahexadecane-1,16-dioxy-dimethacrylate (e.g. Plex 666-1, Röhm), 7,7,9-trimethyl-4,13-dioxo-5,12-diazahexadecane-1,16-dioxy-dimethacrylate (UDMA), urethane (methacrylates) derived from 1,4 and 1,3-Bis(1-isocyanato-1-methylethyl) benzene (e.g. as described in EP 0 934 926 A1 (Ivoclar)) and mixtures thereof.

Also the urethane(meth)acrylates described in WO 2015/006087 (3M) were found to be useful. The content of this reference with respect to the description of the urethane (meth)acrylates is herewith incorporated by reference.

These urethane(meth)acrylates can be characterized as follows:

having the structure A-(-S1-U-S2-MA)$_n$, with

A being a connector element comprising at least one unit,

S1 being a spacergroup comprising at least 4 units connected with each other,

S2 being a spacergroup comprising at least 4 units connected with each other, the units of A, S1 and S2 being independently selected from CH$_3$—, —CH$_2$—, —O—, —S—, —NR$^1$—, —CO—, —CR$^1$=,

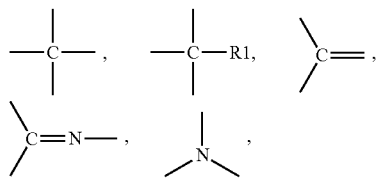

—N=, —CR$^1$R$^2$—, with R$^1$ and R$^2$ independently selected from hydrogen, alkyl, substituted alkyl, alkenyl, cycloalkyl, substituted cycloalkyl, arylalkyl, aryl or substituted aryl, wherein these units can form linear, branched or cyclic structures such as alkyl, cycloalkyl, aryl, ester, urethane or amide groups, U being an urethane group connecting spacergroups S1 and S2, MA being an acrylate or methacrylate group and n being 3 to 6.

According to one embodiment the radiation curable component (B) of the composition can be presented by the structure A-(-S1-U-S2-MA)$_n$ with A being a connector element comprising at least about 1, 2, 3, 4, 5, 6, 7, 8, 9, 10, 11, 12, 13, 14, 15, 16, 17, 18, 19 or 20 units, S1 being a spacergroup comprised of units connected with each other and comprising at least about 4, 5, 6, 7, 8, 9 or 10 units, S2 being a spacergroup comprised of units connected with each other and comprising at least about 4, 5, 6, 7, 8, 9, 10, 12, 15, 20 or 25 units, U being a urethane group connecting spacergroups S1 and S2, MA being an acrylate or methacrylate group and n being about 3 to 6 or about 4 to 6 or about 5 to 6.

It can be preferred, if A has a cyclic structure and comprises at least about 6 units.

It can further be preferred, if S1 has a linear or branched structure and comprises at least about 4 or about 6 units.

It can further be preferred, if S2 has a linear or branched structure and comprises at least about 6 or about 8 units.

A curable component (B), wherein A has a cyclic structure and comprises at least about 6 units and S1 has a linear structure and comprises at least about 4 units and S2 has a linear structure and comprises at least about 8 units and U is an urethane group is sometimes preferred.

Neither the atoms of the urethane group connecting S1 and S2 nor the atoms of the (meth)acrylgroup belong to the spacergroup S1 or S2. Thus, the atoms of the urethane group do not count as units of the spacergroups S1 or S2.

The nature and structure of the connector element is not particularly limited. The connector element can contain saturated (no double bonds) or unsaturated (at least one or two double bonds) units, aromatic or hetero aromatic units (aromatic structure containing atoms including N, O and S). Specific examples of connector element A having a cyclic structure include:

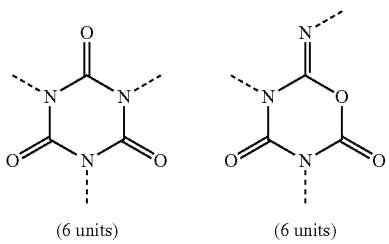

(6 units)   (6 units)

Specific examples of connector element A having a non-cyclic but branched structure include:

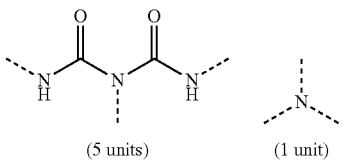

(5 units)   (1 unit)

The dotted lines indicate the bondings to the spacergroup S1. The nature and structure of the spacergroups S1 or S2 is not particularly limited, either.

The spacergroups are comprised of units connected with each other. Typical units include: CH$_3$—, —CH$_2$—, —O—, —S—, —NR$^1$—, —CO—, —CR$^1$=,

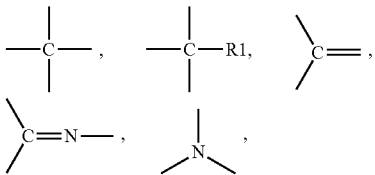

—N=, —CR$^1$R$^2$—, with R$^1$ and R$^2$ independently selected from hydrogen, alkyl, substituted alkyl, alkenyl, cycloalkyl, substituted cycloalkyl, arylalkyl, aryl or substituted aryl.

These units can form linear, branched or cyclic structures such as alkyl, cycloalkyl, aryl, ester, urethane or amide groups.

The structure of S1 can be identical to the structure of S2. However, in some embodiments the structure of S1 is different from S2. In a specific embodiment the number of units being present in S1 is less or equal than the number of units being present in S2.

In a specific embodiment, S1 may have a saturated hydrocarbon structure.

In another specific embodiment, S2 may have a saturated hydrocarbon structure.

Typical examples of useful spacer groups for S1 include:

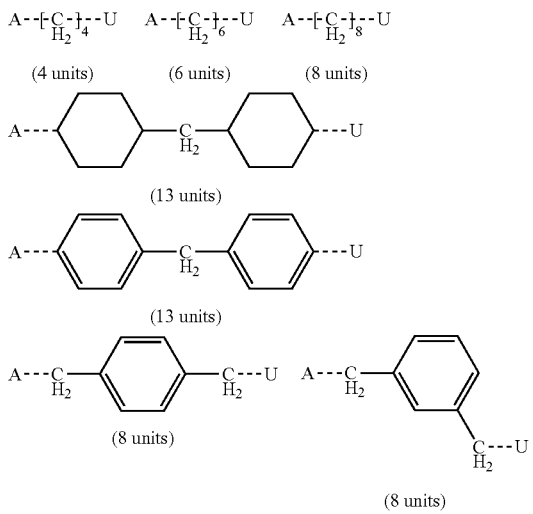

The dotted lines indicate the chemical bonding to either the group A or the group U.

Typical examples of useful spacer groups for S2 include:

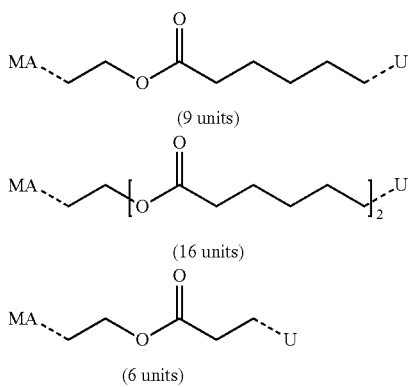

The dotted lines indicate the chemical bonding to either the (meth)acrylate group or the group U. The number of the units to be counted according to the invention is given in brackets.

Generally, it is possible to use the above-mentioned monomers, polymers, and prepolymers alone or as a mixture of two or more of any of these compounds.

The radiation curable component (B) is typically present in the following amounts:

Lower amount: at least 1 or 2 or 3 wt. %;
Upper amount: at most 30 or 20 or 10 wt. %;
Range: from 1 to 30 or from 2 to 20 or from 3 to 10 wt. %;
wt. % with respect to the weight of the whole composition.

The curable composition described in the present text comprises two curing systems: a) a starter (A-S) suitable for curing the cationically curable components (A) and b) a photo-initiator (B-I) for curing the radiation curable components (B).

The ratio of starter (A-S) to photo-initiator (B-I) is typically within a range from 100:1 to 1:1 or from 20:1 to 2:1 with respect to weight.

Thus, the starter (A-S) is typically present in a larger amount compared to the photo-initiator (B-I).

The nature and structure of the starter (A-S) is not particularly limited unless the desired result cannot be achieved.

According to one embodiment, the starter is a component which is water-soluble.

Using a water-soluble starter component can be beneficial, as the starter component will start to dissolve upon contact with water being present in the mixed composition and thus become more effective. There is no need for adding a further dissolvent for dissolving a water-soluble starter component.

According to one embodiment, the starter component is selected from Lewis acids or Broensted acids or precursors of Lewis acids which can be activated by radiation to produce a Lewis acid. In principle both organic and inorganic acids can be used. The starter component is present in the Catalyst Part.

Specific examples of Broensted and Lewis acids, which can be used, include sulfonic acids, phosphonic acids, phosphoric acids, carboxylic acids, antimonic acids, boric acids and mixtures and salts thereof.

Particular useful starters include sulfonium salts, especially alkyl sulfonium salts or sulfonium salts derived from glutaconic acid. Those and others are described e.g. in U.S. Pat. No. 4,167,618 (Schmitt et al.). The content of these documents as regards starters is explicitly mentioned and herewith incorporated by reference.

Suitable sulfonium acids and salts thereof include 4-toluenesulphonic acid, 4-phenolsulphonic acid, 4-bromobenzenesulphonic acid, 4-chlorobenzenesulphonic acid, benzenesulphonic acid, alkylbenzenesulphonic acids, in particular dodecylbenzenesulphonic acid, naphthalene-2-sulphonic acid and alkanesulphonic acids. Other starters which can be used include strong acids such as hexafluoroantimonic acid, hexafluorophosphoric acid or tetrafluoroboric acid.

The use of phosphonic acids such as vinylphosphonic acid and propylphosphonic acid is also possible.

Polymeric acids such as polyvinylphosphonic acid, polyacrylic acid, copolymeric acids, prepared from maleic anhydride with other monomers can also be used, if desired.

Furthermore, saturated and unsaturated carboxylic acids such as propionic acid, succinic acid, tartaric acid, trimellitic acid, benzoic acid, phenylacetic acid, citric acid, maleic acid, adipinic acid, o-chlorobenzoic acid or reaction products of polyvalent alcohols and acid anhydrides such as maleic anhydride and succinic anhydride can also be used.

Those and other starters are described e.g. in US 2003/153726 (Eckhardt et al.).

The content of this document as regards starters for cationically curable components is explicitly mentioned and herewith incorporated by reference.

The starter component being present in the Catalyst Part is typically present in the following amounts:

Lower amount: at least 1 or 2 or 3 wt. %;
Upper amount: at most 30 or 20 or 10 wt. %;
Range: from 1 to 30 or from 2 to 20 or from 3 to 10 wt. %;
wt. % with respect to the weight of the whole composition.

The curable composition described in the present text comprises a photo-initiator. The photo-initiator is present in the Catalyst Part of the curable composition.

However, the photo-initiator may also be present in the Base Part of the curable composition or in both parts.

If desired, the photo-initiator can be characterized by one or more of the following features:
- comprising an alpha-diketon component and/or phosphine oxide component;
- having an absorption band in the range from 300 to 800 nm or from 400 to 700 nm;
- molecular weight: from 50 to 1,000 g/mol or from 100 to 800 g/mol.

The photo-initiator should be partly, essentially or completely soluble in the curable composition, free of functionalities that would substantially interfere with the cationic polymerization process, and capable of light absorption somewhere within the range of wavelengths between 300 and 800 nanometers (nm). Preferred visible photo-initiators contain one or more carbonyl functional groups.

Using alpha-diketones as photo-initiators are sometimes preferred for dental applications.

Examples of preferred photo-initiators are selected from camphorquinone; glyoxal; biacetyl; 3,3,6,6-tetramethylcyclohexanedione; 3,3,7,7-tetramethyl-1,2-cycloheptanedione; 3,3,8,8-tetramethyl-1,2-cyclooctanedione; 3,3,18,18-tetramethyl-1,2-cycloocta-decanedione; dipivaloyl; benzil; furil; hydroxybenzil; 2,3-butanedione; 2,3-pentanedione; 2,3-hexanedione; 3,4-hexanedione; 2,3-heptanedione; 3,4-heptanedione; 2,3-octanedione; 4,5-octanedione; 1,2-cyclohexanedione; and 1-phenyl-1,2-propanedione; and mixtures thereof. Of these, camphorquinone is the most preferred photo-initiator.

Alternatively, free-radical initiators which can be used include the class of phosphine oxide components including acylphosphine oxides and bisacylphosphine oxides.

Suitable acylphosphine oxides can be described by the general formula

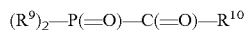

$(R^9)_2\text{—}P(\!=\!O)\text{—}C(\!=\!O)\text{—}R^{10}$ wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S-, O-, or N-containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms. Preferred acylphosphine oxides are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Examples can also be found e.g. in U.S. Pat. No. 4,737,593 (Ellrich et al.).

Suitable bisacylphosphine oxides can be described by the general formula

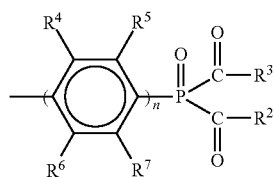

wherein n is 1 or 2, and $R^4$, $R^5$, $R^6$ and $R^7$ are H, $C_{1-4}$ alkyl, $C_{1-4}$ alkoxyl, F, $C_1$ or Br; $R^2$ and $R^3$, which are the same or different, stand for a cyclohexyl, cyclopentyl, phenyl, naphthyl, or biphenylyl radical, a cyclopentyl, cyclohexyl, phenyl, naphthyl, or biphenylyl radical substituted by F, Cl, Br, I, $C_{1-4}$ alkyl and/or $C_{1-4}$ alkoxyl, or an S or N-containing 5-membered or 6-membered heterocyclic ring; or $R^2$ and $R^3$ are joined to form a ring containing from 4 to 10 carbon atoms and being optionally substituted by 1 to 6 $C_{1-4}$ alkyl radicals.

Further examples include: bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-ethoxyphenylphosphine oxide, bis-(2,6-dichlorobenzoyl)-4-biphenylylphosphine oxide, bis-(2,6-dichlorobenzoyl)-4-propylphenylphosphine oxide, bis-(2,6-dichlorobenzoyl)-2-naphthylphosphine oxide, bis-(2,6-dichlorobenzoyl)-1-napthylphosphine oxide, bis-(2,6-dichlorobenzoyl)-4-chlorophenylphosphine oxide, bis-(2,6-dichlorobenzoyl)-2,4-dimethoxyphenylphosphine oxide, bis-(2,6-dichlorobenzoyl)decylphosphine oxide, bis-(2,6-dichlorobenzoyl)-4-octylphenylphosphine oxide, bis-(2,6-dimethoxybenzoyl)-2,5-dimethylphenylphosphine oxide, bis-(2,6-dimethoxybenzoyl)phenylphosphine oxide, bis-(2,4,6-trimethylbenzoyl)-2,5-dimethylphenylphosphine oxide, bis-(2,6-dichloro-3,4,5-tri-methoxybenzoyl)-2,5-dimethylphenylphosphine oxide, bis-(2,6-dichloro-3,4,5-trimethoxybenzoyl)-4-ethoxyphenylphosphine oxide, bis-(2-methyl-1-naphthoyl)-2,5-dimethylphenylphosphine oxide, bis-(2-methyl-1-naphthoyl)phenylphosphine oxide, bis-(2-methyl-1-naphthoyl)-4-biphenylylphosphine oxide, bis-(2-methyl-1-naphthoyl)-4-ethoxyphenylphosphine oxide, bis-(2-methyl-1-naphthoyl)-2-naphthylphosphine oxide, bis-(2-methyl-1-naphthoyl)-4-propylphenylphosphine oxide, bis-(2-methyl-1-naphthoyl)-2,5-dimethylphosphine oxide, bis-(2-methoxy-1-naphthoyl)-4-ethoxyphenylphosphine oxide, bis-(2-methoxy-1-naphthoyl)-4-biphenylylphosphine oxide, bis-(2-methoxy-1-naphthoyl)-2-naphthylphosphine oxide and bis-(2-chloro-1-naphthoyl)-2,5-dimethyl-phenylphosphine oxide.

The acylphosphine oxide bis(2,4,6-trimethylbenzoyl)phenyl phosphine oxide (IRGACURE™ 819, Ciba Specialty Chemicals, Tarrytown, NY) is sometimes preferred.

Tertiary amine reducing agents may be used in combination with an acylphosphine oxide. Illustrative tertiary amines which can be used include ethyl 4-(N,N-dimethyl-amino) benzoate and N,N-dimethylaminoethyl methacrylate.

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis(η5-2,4-cyclopentadien-1-yl)-bis (2,6-difluoro-3-(1H-pyrrol-1-yl)phenyl) titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, NC).

According to one embodiment, the curable composition described in the present text does not comprise iodonium initiators in an amount of more than 0.1 wt. % with respect to the whole composition.

The amount of photo-initiator to be used is not particularly limited, unless the desired curing reaction cannot be achieved.

The photo-initiator being present in the Catalyst Part is typically present in the following amounts:

Lower amount: at least 0.01 or 0.1 or 0.2 wt. %;
Upper amount: at most 3 or 2 or 1 wt. %;
Range: from 0.01 to 3 or from 0.1 to 2 or from 0.2 to 1 wt. %;

wt. % with respect to the weight of the whole composition.

According to a further embodiment, the curable composition described in the present text comprises one or more accelerators.

Using an accelerator can be beneficial for enhancing the efficiency of the photo-initiator.

The accelerator often acts as a kind of reducing agent for the photo-initiator.

Suitable accelerators typically have an amine moiety. In particular useful are secondary and tertiary aliphatic or aromatic amines.

Suitable examples of the tertiary amines include N,N-dimethylaminoethyl methacrylate, ethyl 4-dimethylaminobenzoate, methyl 4-dimethylaminobenzoate, triethanolamine, N,N-dimethyl-p-toluidine, and isoamyl 4-dimethylaminobenzoate.

The amount of accelerator which can be used is not particularly limited, unless the desired curing reaction cannot be achieved.

If present, the accelerator is typically present in the following amounts:

Lower amount: at least 0.1 or 0.2 or 0.5 wt. %;
Upper amount: at most 5 or 3 or 2 wt. %;
Range: from 0.1 to 5 or from 0.2 to 3 or from 0.5 to 2 wt. %;

wt. % with respect to the weight of the whole composition.

The molar ratio between the photo-initiator and the accelerator includes ranges from 10:1 to 1:10 or from 4:1 to 1:4.

The curable composition described in the present text may also contain filler(s).

A wide variety of inorganic, hydrophilic or hydrophobic fillers may be employed such as silicas, aluminas, magnesias, titanias, inorganic salts, metallic oxides, quartz, cristobalit, kaolin, talcum, feldspar, wollastonit, nephelinsyenit, silicates and glasses. It has been found to be possible to employ mixtures of silicone dioxides, such as a diatomaceous earth and/or fumed silica. Those filler are commercially available from companies like Degussa/Evonik or Wacker under the trade names Aerosil™, HDK-H, HDK 2050.

The following commercially available fillers were found to be particularly useful: quartz comprising amino-silane groups (e.g. Silbond™ 600 AST, Silbond™ 800 AST; Quarzwerke Frechen), wollastonite comprising amino-silane groups (e.g. Tremin™ 283-600 AST or Tremin™ 939-300 AST; Quarzwerke Frechen), quartz/kaolin mixture comprising amino-silane groups (e.g. Aktisil™ AM; Quarzwerke Frechen), quartz comprising epoxy groups (e.g. Silbond™ 600 EST, Silbond™ 800 EST; Quarzwerke Frechen) and quartz comprising trimethyl-silane groups (e.g. Silbond™ 800 RST).

More specifically, fillers which can be used include calcium silicate, diatomaceous earth, zirconium silicate, montmorillonite such as bentonite, barium sulphate, calcium carbonate, plaster, glass and plastic powder.

The sizes and surface areas of the foregoing materials can be adjusted to control the viscosity and thixotropicity of the resulting compositions.

A combination of reinforcing and non-reinforcing fillers sometimes even further improves the rheology of the un-cured composition and the elasticity of the cured composition.

Typical reinforcing fillers include fumed silica, carbon black and the like. They also can improve mechanical properties like tensile strength or tear strength, of the cured silicone composition.

Typical non-reinforcing fillers include precipitated silica, diatomaceous earth, alumina, magnesia, titanium dioxide, zirconium silicate and mixtures and combinations thereof.

If present, filler is typically present in the following amounts:

Lower amount: at least 1 or 5 or 10 wt. %;
Upper amount: at most 70 or 60 or 50 wt. %;
Range: from 1 to 70 or from 5 to 60 or from 10 to 50 wt. %;

wt. % with respect to the weight of the whole composition.

If the amount of the filler is too low, a desired Shore hardness might not be obtained.

If the amount of the filler is too high, the elasticity of the cured composition might negatively be affected and the viscosity of the un-cured composition might be too high. Moreover, the shelf life might negatively be influenced.

Besides surface-treated fillers, non-surface treated fillers can be added. A "non-surface treated filler" in the present context is a filler having a surface which has not been exposed to reactive substances resulting in a modification of the surface of the filler to make the filler more compatible with other components of the composition.

Filler(s) may be present in either the Catalyst Part or the Base Part or in both parts, Catalyst Part and Base Part.

The curable composition may also include one or more surfactant(s), especially Si-containing surfactant(s) or mixture of Si-containing surfactants.

If surfactant(s) are present they are typically present in an amount sufficient and not detrimental to the desired effect or effects to be achieved.

Surfactants or hydrophilizing agents which can be employed can generally be chosen freely from all types of surfactants which improve the hydrophilicity of a polyether group containing polymer.

Preferably, the use of the surfactant should not negatively impact the material properties or curing behavior of the curable composition or at least not more than avoidable or tolerable.

Surfactant(s) can comprise an agent or a plurality of agents which are generally capable of increasing the hydrophilic character to a composition, for example as demonstrated by a decrease in the wetting angle of a drop of water or an aqueous solution or dispersion (e.g. a plaster suspension or the like) on the material (in its cured or uncured state).

In certain embodiments, the surfactant does not contain reactive groups so that it is not incorporated into the network of the hardenable composition.

Useful surfactants also include polyether carbosilanes of the following formula:

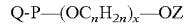

in which Q stands for $R_3Si$— or $R_3Si$—$(R'$—$SiR_2)_a$—$R'$—$SiR'_2$—, where every R in the molecule can be the same or different and stands for an aliphatic $C_1$-$C_8$, a cycloaliphatic $C_6$-$C_{12}$ or an aromatic $C_6$-$C_{12}$ hydrocarbon radical, which can optionally be substituted by halogen atoms, R' is a $C_1$-$C_{14}$ alkylene group, R" is R in the case of a≠0 or is R or $R_3SiR'$ in the case of a=0, and a=0-2; P stands for a $C_2$-$C_{18}$ alkylene group, preferably a $C_2$-$C_{14}$ alkylene group or A-R''', where A represents a $C_2$-$C_{18}$ alkylene group and R''' a functional group selected from: —NHC(O)—, —NHC(O)—$(CH_2)_{n-1}$—, —NHC(O)C(O)—, —NHC(O)$(CH_2)_v$C(O)—, —OC(O)—, —OC(O)—$(CH_2)_{n-1}$—, —OC(O)C(O)—, —OC(O)$(CH_2)_v$C(O)—, —OCH$_2$CH(OH)CH$_2$OC(O)$(CH_2)_{n-1}$—, —OCH$_2$CH(OH)CH$_2$OC(O)$(CH_2)_v$C(O)— with v=1-12; Z is H or stands for a $C_1$-$C_4$ alkyl radical or a $C_1$-$C_4$ acyl radical; x stands for a number from 1 to 200 and n stands for an average number from 1 to 6, preferably 1 to 4. Thus, the element —SiR'''$_2$-can also comprise the substructure —Si(R)(R$_3$SiR')—.

Other surfactants which can be used, either alone or as a mixture of two or more thereof, can be found in U.S. Pat. No. 4,657,959 (Bryan et al.), col. 4, l. 46 to col. 6. l. 52 as well as in EP 0 231 420 B1 (Gribi et al.; also published as AU 6,857,087) p 4, l. 1 to p 5, l. 16 and in the examples.

U.S. Pat. Nos. 5,750,589, 4,657,959 and EP 0 231 420 B1 are expressly described and cited herein as a source of disclosure for compounds which can be used as component (E1) according to the invention.

Some of the surfactants, which can be used can be summarized under the following formula:

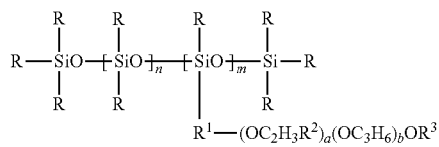

where each R is independently a monovalent hydrocarbyl radical with 1 to 22 C-atoms, $R^1$ is a divalent hydrocarbylene radical 1 to 26 C-atoms, each $R^2$ is independently hydrogen or a lower hydroxyalkyl radical, $R^3$ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition of the invention has the desired water contact angle.

Preferably R and $R^3$ are —CH$_3$, $R^1$ is —C$_3$H$_6$—, $R^2$ is hydrogen, n is zero or one, m is one to five, a is five to 20 and b is 0.

Several of such ethoxylated surfactants are for example available from Momentive Performance Materials Inc. including "SILWET™" surface active copolymers. Preferred surface active copolymers include Silwet 35, Silwet L-77, Silwet L-7600 and Silwet L-7602, Silwet L-7608 and Silwet Hydrostable 68 and Silwet Hydrostable 611. Silwet L-77 is an especially preferred ethoxylated surfactant which is believed to correspond to the above formula where R and $R^3$ are —CH$_3$, $R^1$ is —C$_3$H$_6$—, $R^2$ is hydrogen, n is zero or one, m is one or two, a is seven, and b is 0. Also possible is the use of MASIL™ SF19, as obtainable from Lubrizol performance products, Spartanburg, US.

Examples of useful non-ionic surfactants include those according to the following formula:

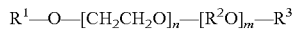

wherein $R^1$ represents hydrogen or an aromatic or aliphatic, linear or branched hydrocarbon group having 1-20 carbon atoms, $R^2$ represents an alkylene having 3 carbon atoms, $R^3$ represents hydrogen or a $C_1$-$C_3$ alkyl group, n has a value of 0 to 40, m has a value of 0 to 40 and the sum of n+m being at least 2.

It will be understood that in the above formula, the units indexed by n and m may appear as blocks or they may be present in an alternating or random configuration. Examples of non-ionic surfactants according to the formula above include alkylphenol oxethylates such as ethoxylated p-isooctylphenol commercially available under the brand name TRITON™ such as for example TRITON™ X 100 wherein the number of ethoxy units is 10 or TRITON™ X 114 wherein the number of ethoxy units is 7 to 8.

Still further examples include those in which $R^1$ in the above formula represents an alkyl group of 4 to 20 carbon atoms, m is 0 and $R^3$ is hydrogen. An example thereof includes isotridecanol ethoxylated with 8 ethoxy groups and which is commercially available as GENAPOL™ X080 from Clariant GmbH.

Non-ionic surfactants according to the above formula with $R^1$ and $R^3$ representing a $C_1$-$C_3$ alkyl chain or hydrogen and in which the hydrophilic part comprises a block-copolymer of ethoxy groups and propoxy groups may be used as well. Such non-ionic surfactants are commercially available from Clariant GmbH under the trade designation GENAPOL™ PF 40 and GENAPOL™ PF 80. Further suitable non-ionic surfactants that are commercially available include Tergitol™ TMN 6, Tergitol™ TMN 10, or Tergitol™ TMN 100X. Also statistical, alternating or block copolymers of ethylene oxide and propylene oxide are suitable surfactants according to the present invention. Such non-ionic surfactants are available e.g. under the trade name Breox™ A, Synperonic™ or Pluronic™.

The composition described in the present text may also comprise in addition to other ingredients and surfactants, alone or in combination an F-containing component including those described in EP application number 09162681.2, especially those described on pages 21 to 27.

According to a further embodiment, the curable composition described in the present text can also comprise one or more additives.

Suitable additives include pigment(s), stabilizer(s), plasticiser(s), liquid(s), diluting agent(s), triacyl esters of glycerol, astringent(s), retarder(s) and other ingredients well known to those skilled in the art.

The amounts and types of each ingredient in the composition should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

Examples for pigments include titanium dioxide or zinc sulphide (lithopones), red iron oxide 3395, Bayferrox™ 920 Z Yellow, Neazopon™ Blue 807 (copper phthalocyanine-based dye) or Helio™ Fast Yellow ER.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyani sole (2,6-di-tert-butyl-4-ethoxyphenol), 2,6-di-tert-butyl-4-(dimethylamino)methylphenol, 4-methoxybenzylalcohol, 2,6-di-tert.-butyl-4-methylphenol ("Jonol"), 3-methoxyphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryl-oxyethylphenyl)-2H-benzotriazole, phenothiazine, tocopherol, polyethylene imine, substituted pyridines (e.g. 2,6-di-tert.-butyl-4-methylpyridine) and HALS (hindered amine light stabilizers). Such adjuvants may optionally comprise reactive functionality so that they will be copolymerized with the resin.

All kinds of known and compatible softeners and rheology modifiers like non-reactive polymeric fluids or fats commonly used in commercialized impression materials can be added. Preferred are those ingredients and additives that do not add unpleasant smell or taste. Compounds that have an unpleasant smell might be removed by thinfilm evaporation, if needed.

Typical plasticisers include, e.g., compounds of the ester type such as $C_{12}$- to $C_{15}$-alkyl lactates, ethyl or butyl esters of citric acid or of acetylcitric acid, phthalic acid esters of relatively long, branched alcohols such as bis(2-ethylhexyl) phthalate or phthalic acid polyester, $C_2$- to $C_{22}$-dialkyl esters of $C_2$- to $C_6$-dicarboxylic acids such as bis(2-ethylhexyl) adipate, dioctyl maleate, diisopropyl adipate, aromatic and aliphatic sulfonic acid esters such as $C_2$- to $C_{20}$-alkylsulfonic acid esters of phenol or of $C_1$- to $C_{22}$-alkanols or aromatic plasticisers such as polyphenyls in a wide viscosity range, including wax-like polyphenyls such as are obtainable, for example, from the Monsanto company, isomeric mixtures of $C_{20}$ to $C_{40}$ aromatic compounds, with preference being given to the use of mixtures of plasticisers of the ester type and aromatic type.

Liquids such as $C_{12}$-$C_{15}$ alkyl acetates, liquid derivatives of citric acid, esters of phthalic acid with branched alcohols like bis(2-ethylhexyl)phthalate or polymeric phthalates, $C_2$-$C_{18}$ bis(alkyl)esters of $C_2$-$C_6$ dicarboxylic acids like dioctylmaleate, dioctyladipate, aromatic and aliphatic esters of sulfonic acids like Mesamoll™, typical aromatic diluters like poly phenyls, xylyl toluene, and dixylyl toluene can be used. Also low molecular weight alcohols that may contain more than one OH-function like propane-1,2-diol may be used. From the group of polymeric compounds, polypropylene glycols and its derivatives are sometimes preferred.

An example of a preferred plasticiser combination is a mixture of acetyl tributyl citrate and dibenzyltoluene.

Suitable diluting agent(s) usually do not contain reactive moieties like —SH or —COOH, primary or secondary amino groups, but may contain —OH. Liquids such as $C_{12}$-$C_{15}$ alkyl acetates, liquid derivatives of citric acid, esters of phthalic acid with branched alcohols like bis(2-ethylhexyl)phthalate or polymeric phthalates, $C_2$-$C_{18}$ bis(alkyl) esters of $C_2$-$C_6$ dicarboxylic acids like dioctylmaleate, dioctyladipate, aromatic diluters like poly phenyls, dibenzyl toluene, xylyl toluene, dixylyl toluene and polymeric compounds like polyethers, polyesters, polycarbonates, polytetrahydrofuranes, polyolefines can be used. Also low molecular weight alcohols that may contain more than one OH-function like propane-1,2, diol or carbonates like propylene carbonate may be used. From the group of polymeric compounds, polypropylene glycols and its derivatives are preferred.

Likewise suitable as additives are triacyl esters of glycerol of non-animal origin. Suitable additives can consist of, for example, modified fats of vegetable origin such as hydrogenated palm oil or soybean oil or synthetic fats.

Suitable fats are described in U.S. Pat. No. 6,395,801, to the full content of which reference is here made. Avocado oil, cottonseed oil, groundnut oil, cocoa butter, pumpkin seed oil, linseed oil, maize germ oil, olive oil, palm oil, rice oil, rapeseed oils, safflower oil, sesame oil, soybean oil, sunflower oil, grapeseed oil, wheat germ oil, Borneo tallow, fulwa butter, hemp oil, illlipe butter, lupin oils, candlenut oil, kapok oil, katiau fat, kenaf seed oil, kekuna oil, poppy seed oil, mowrah butter, okra oil, perilla oil, sal butter, shea butter and tung oil are especially suitable, provided that the fats in question have been hydrogenated before use. Suitable hydrogenated fats are considered to be those whose iodine value is less than 20 (measured in accordance with the DGF [German Society for Fat Science] standard C-V 11 Z2). Fat hydrogenation procedures are described, for example, in "Ullmanns Enzyklopadie der industriellen Chemie", 4th edition, volume 11, p. 469.

Mixtures of naturally occurring fats, and also synthetically prepared fats such as Softisan™ 154 or Dynasan™ 118 (from Huls Comp.) can likewise be used. The preparation of such synthetic triacyl glycerides is known to the person skilled in the art and can be carried out by starting from glycerol and the appropriate fatty acid methyl esters.

Preferred triacyl glycerides correspond to the following formula:

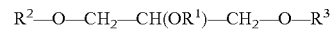

in which $R^1$, $R^2$ and $R^3$ denote, each independently of the others, $C_{11}H_{23}CO$, $C_{13}H_{27}CO$, $C_{15}H_{31}CO$ or $C_{17}H_{35}CO$. Mixtures of such triacyl glycerides can also be used.

Astringent(s) which may be included comprise aluminum salts like aluminum sulfate, aluminum ammonium sulfated, aluminum chlorohydrated, aluminum acetate and mixtures thereof. Useful astringent(s) can also contain iron or manganese containing substances.

Incorporating an astringent may help to prevent or reduce the risk of bleeding during use or after removal of the composition from the mouth of a patient.

If additive(s) are present, they are typically present in an amount sufficient and not detrimental to the desired effect or effects to be achieved.

Additive(s) (F) may be present in the Catalyst Part or the Base Part or in both parts, the Catalyst Part and the Base Part.

If present, the additive(s) are typically present in the following amounts:
Lower amount: at least 0.005 or 0.01 or 0.1 wt. %;
Upper amount: at most 50 or 40 or 30 wt. %;
Range: from 0.005 to 50 or from 0.01 to 40 or from 0.1 to 30 wt. %;
wt. % with respect to the weight of the whole composition.

The components are typically present in in the following amounts:
cationically curable components from 5 to 90 wt. % or from 12 to 85 wt. %,
radiation curable components from 1 to 30 wt. % or from 2 to 20 wt. %,
starter from 1 to 30 wt. % or from 2 to 20 wt. %, and
photo-initiator from 0.01 to 3 wt. % or from 0.1 to 2 wt. %,
accelerator from 0 to 5 wt. % or from 0.1 to 3 wt. %,
filler(s) from 0 to 70 wt. % or from 5 to 60 wt. %,
additive(s) from 0 to 50 wt. % or from 0.01 to 40 wt. %,
wt. % with respect to the weight of the whole composition.

The present invention is also directed to the cured composition obtained after curing the curable composition described in the present text.

The cured composition can typically be characterized by one or more of the following features:

Shore hardness A: from 40 to 90 or from 50 to 90, after exposure to light and if determined according to DIN 53505:2000-8 24 h after mixing the Base Part and the Catalyst Part;

Tensile strength: above 1 MPa or above 2 MPa or above 3 MPa, after exposure to light and if determined according to DIN 53504:2015-08, 24 h after mixing the Base Part and the Catalyst Part.

Being rubber elastic;

Consistency: below 40 mm or below 35 mm or below 30 mm or below 25 mm according to ISO 4823:2015-08.

If desired, these parameters can be determined as described in the example section.

The cured composition comprises two different polymeric networks.

One polymeric network is based on the crosslinking of the cationically curable components.

The other polymeric network is based on the crosslinking of the radiation curable components.

The curable composition described in the present text comprises a curing system comprising
 a starter suitable for curing cationically curable components,
 a photo-initiator comprising an alpha-diketon and/or phosphine oxide component and
 an amine accelerator,
wherein the components are as described the present text.

Such a curing system is useful for curing a composition comprising cationically curable components and radiation curable components like those described in the present text.

Due to the presence of two separate curing systems, the curing behaviour of the composition to be cured can be adjusted. In particular, upon application of radiation the viscosity of the curable composition can be increased on demand.

The curable composition described in the present text can be produced by mixing the respective components, e.g. by using a speed mixer or a kneading machine. Due to the presence of a photo-initiator system, the mixing or kneading is typically carried out under safe-light conditions to avoid an early undesired curing of the composition.

Suitable inert solvents may be employed when formulating this mixture. Any solvent may be used which does not react appreciably with the components of the inventive compositions. Examples of suitable solvents include acetone, dichloromethane, acetonitrile, propylene carbonate, poly-THF and lactones (e.g. gamma-butyrolactone).

The curable composition described in the present text is provided in separate parts before use. This is beneficial for improving the storage stability and/or shelf life.
When used, the components of the different parts are mixed in the suitable amounts and applied using conventional techniques.

Providing a base paste and a catalyst paste with nearly equal viscosities may facilitate the mixing to obtain a homogeneous composition, especially if the mixing is done using a static mixing tip.

The volume ratios of catalyst paste and base paste can range from 10:1 to 1:10. Particularly preferred volume ratios of base paste to catalyst paste are from 1:1 to 10:1 or from 2:1 to 5:1 (e.g. 5 parts of base paste to 1 part of catalyst paste) or from 2:1 to 4:1.

The curable composition described in the present text is typically stored in a container until use.

If the composition is applied into the sulcus of a teeth (i.e. the region between gum and hard dental tissue), using a container with a nozzle as shown and described in WO 2009/151983 A2 can be beneficial due to its specific geometry.

Cartridges which can also be used are described e.g. in US 2007/0090079 (Keller) or U.S. Pat. No. 5,918,772 (Keller et al.). Cartridges which can be used are commercially available from SulzerMixpac AG (Switzerland).

Other suitable devices can be found in WO 2005/016783 A1 (3M), WO 2007/047381 (3M), WO 2007/104037 (3M), and WO 2009/061884 (3M). The content of these documents is herewith incorporated by reference. If desired, the composition can also be stored in foil bags.

In practice, the curable composition provided as a two-component system is syringed through a static or dynamic mixing device.

The curable composition can be applied onto a surface or into an impression tray or onto the patients' teeth or tissue (including sulcus) and placed in the patients' mouth. The curable composition may also be applied using an applicator like an elastomer syringe.

The invention is also directed to a process of curing the curable composition as described in the present text, the process comprising the steps of
 mixing the Base Part and the Catalyst Part of the curable composition as described in the present text,
 applying the curable composition to a surface,
 applying radiation to the curable composition,
wherein the application of radiation can be done either during mixing or during application of the curable composition to a surface, after the application of the curable composition to a surface, or a combination thereof.

According to one embodiment, the application of radiation during mixing of the composition is preferred.

The surface can be dental surface or a non dental surface.

According to one embodiment the curable composition described in the present text is not only suitable as dental impression material but also as dental retraction material.

The hardenable composition can not only be easily placed in the sulcus of a tooth, but also exerts sufficient pressure on the surrounding soft tissue having the result that the sulcus is widened. Due to its elastomeric properties in its cured stage, the composition can also be easily removed from the sulcus after hardening.

If used in the dental field, curing is preferably carried out at a temperature below 50° C. and preferably below 40° C.

A typical time for cure of curable compositions as described in the present text used for dental applications is within 20 min, or preferably within 10 min, after mixing the components of the composition.

The material is generally regarded as cured, if the cured material fulfils the requirements for its use. For example, a dental precision impression material typically fulfils the requirements for its use when it fulfils the requirements of ISO 4823:2015-08 (such as compatibility with gypsum, strain in compression, recovery from deformation, detail reproduction, linear dimensional change).

The invention is also directed to a process for taking a dental impression including sub-gingival parts and/or conducting a dental retraction.

Such a process typically comprises the steps of
 combining the Base Part and the Catalyst Part of the curable composition as described in any of claims 1 to 12 to obtain a curable composition,
 applying a portion X of the curable composition to the surface of dental tissue, in particular into the sulcus of a tooth, wherein radiation is applied to the portion X of the curable composition either during or at the end of the combining step, optionally applying radiation to the portion X of the curable composition after it has been applied to the dental tissue, applying a portion Y of the curable composition in contact with portion X of the curable composition to which radiation has been applied, optionally applying a dental impression material being different from the curable composition in contact with the curable composition, wherein the optionally applied dental impression material can also be applied to a partially hardened curable composition, removing the composition and the optionally applied dental impression material from the dental tissue.

Conducting the above described process can help to reduce and thus simplify the steps to be conducted by the practitioner during a dental impression and/or dental retraction procedure where the recording of the surface of the dental tissue beyond the gumline is desired and/or needed.

The volume of portion X is typically lower than the volume of portion Y.

A typical volume for portion X is from 0.1 to 2 ml or from 0.2 to 1 ml.

A typical volume for portion Y is from 2 ml to 20 ml or from 3 ml to 10 ml.

The above volumes relate to the amount of material typically used for the treatment of one tooth.

The curable composition is typically applied into the sulcus of a prepared dental situation (i.e. tooth) and exerts pressure on the surrounding tissue.

After hardening of the curable composition, a further portion of the same curable composition is applied on top of the visible surface of the previously applied composition.

However, as no radiation was applied to the further portion of the curable composition, this portion of the curable composition has a different viscosity, i.e. a lower viscosity.

The optionally applied dental impression material can facilitate the removal process of the cured composition from the tooth surface, e.g. it allows the simultaneous removal of cured compositions from the sulcus of different teeth.

According to a further embodiment, the process comprises the following steps:

combining the Base Part and the Catalyst Part of the curable composition as described in the present text to obtain a curable composition, applying a portion X of the curable composition to the surface of dental tissue, in particular into the sulcus of a tooth, applying radiation to this portion X of the curable composition, applying a portion Y of the curable composition in contact with portion X of the curable composition to which radiation has been applied, letting both portions X and Y of the composition harden, applying a dental impression material being different from the curable composition in contact with the cured composition, and letting the dental impression material harden, removing the hardened composition and the dental impression material from the dental tissue.

According to a further embodiment, the process comprises the following steps:

combining the Base Part and the Catalyst Part of the curable composition as described in the present text to obtain a curable composition, applying a portion X of the curable composition to the surface of dental tissue, in particular into the sulcus of a tooth, applying radiation to this portion X of the curable composition, applying a portion Y of the curable composition in contact with portion X of the curable composition to which radiation has been applied, applying a dental impression material being different from the curable composition in contact with the curable composition, letting both portions X and Y of the composition and the dental impression material harden, removing the hardened composition and the dental impression material from the dental tissue.

In all cases radiation can be applied to the curable composition either before or after application of the curable composition to the surface of dental tissue. Alternatively or in addition, radiation can be applied to the combined portions X and Y.

However, applying radiation before is typically more advantageous as the curable composition is already in a pre-cured state and thus having a lower viscosity. Usually, such a paste can be applied into the sulcus of a tooth more easily.

Depending on the thickness and transparency of the composition to be cured, radiation is typically applied for a time period ranging from a few seconds to a few minutes, e.g. from 1 s to 120 s or from 5 s to 60 s from 10 s to 40 s.

The following combination of parameters was found to be particularly effective:

Wavelength: from 400 to 500 nm;
Duration: from 2 s to 2 min or from 10 s to 1 min;
Power: from 300 mW/cm$^2$ to 2500 mW/cm$^2$.

The exposure of the composition to radiation can be repeated, if desired.

Curing of the composition is typically done at ambient temperature or a temperature which is typically present in the mouth of a patient (e.g. within a range from 15 to 40° C.) and at ambient pressure (e.g. within a range from 850 to 1,100 hPa).

The dental impression material mentioned above is typically a composition being obtainable or obtained upon combining a base paste and a catalyst paste, wherein the components of the base and catalyst paste are the same as described in the present text for Base Part and Catalyst Part, except for the presence of the radiation curable component(s) (B) and the photo-initiator (B-I).

However, the dental impression material typically differs from the curable composition with respect to at least one or more or all of the following features:

consistency according to ISO 4823:2015-08;
filler content.

The consistency according to ISO 4823:2015-08 of the dental impression material is typically higher in mm (meaning lower viscosity), e.g. by at least 2 mm compared to the consistency according to ISO 4823:2015-08 of the curable composition described in the present text.

According to one embodiment, the invention is directed to a curable composition comprising a resin matrix, the resin matrix comprising
cationically curable components (A) comprising an aziridino moiety, and radiation curable components (B) comprising a (meth)acrylate moiety and an urethane moiety,
optionally comprising filler(s),
optionally comprising surfactant(s),
optionally comprising an accelerator,
a curing system, the curing system comprising
a starter (A-S) suitable for curing the cationically curable components (A) being selected from Lewis acids, Broensted acids or precursors of Lewis acids, Broensted acids, or a mixtures thereof
and
a photo-initiator (B-I) selected from alpha-diketon and/or phosphine oxide components,
the curable composition being provided as a Base Part and Catalyst Part being separated before use,
wherein the Base Part comprises components (A) and (B) and
wherein the Catalyst Part comprises components (A-S) and (B-I), and
wherein the respective components are described in the present text.

According to another embodiment, the invention is also directed to the composition described above for use in a process for taking a dental impression including sub-gingival parts, wherein the respective components are described in the present text.

The invention is also directed to a kit of parts comprising the curable composition as described in the present text together with one or more of the following items alone or in combination:
dental impression material being different from the curable composition with respect to composition or packaging;
application device for applying the curable composition;
radiation source, in particular a dental curing light.

A suitable application device typically comprises a static or dynamic mixing tip suitable for mixing the Base Part and the Catalyst Part of the curable composition. The mixing tip typically has a shape and dimension enabling the application of the curable composition into the sulcus of a tooth.

In the dental and orthodontic area suitable commercially dental curing lights are sold e.g. under the trade name Elipar™ Freelight or Elipar™ S10 (3M Oral Care/3M ESPE).

All components used in the curable composition of the present text should be sufficiently biocompatible, that is, the composition should not produce a toxic, injurious, or immunological response in living tissue.

Features and advantages of this invention are further illustrated by the following examples. The Examples are in no way intended to be limiting thereof. The particular materials and amounts thereof recited in these examples, as well as other conditions and details, should not be construed to unduly limit this invention.

EXAMPLES

Unless otherwise indicated, all parts and percentages are on a weight basis, all water is deionized water, and all molecular weights are weight average molecular weight. Moreover, unless otherwise indicated all Experiments were conducted at ambient conditions (23° C.; 1013 mbar).
Light Source
Unless otherwise indicated all experiments that require radiation with light are done using a standard dental light source, either (Elipar™ S10, 3M) or Visio™ Beta (3M).

The Elipar™ S10 light source emitts radiation predominantly in the range of 430-480 nm and has a light intensity of about 1200 mW/cm$^2$. The Visio™ Beta light source was used for larger specimens, that can't be exposed to light homogeneously using a hand held Elipar™ device. The Visio™ Beta device was only used applying Program 1 without vacuum (exposure time 1 min).
Measurements
Consistency
Consistency of the composition was determined on the basis of ISO 4823:2015-08 with the following changes. The weight load is applied to all specimens 45 sec. after the end of the mixing. In case light radiated specimens are to be measured, the light radiation takes place between 25 sec. and 35 sec. after the end of mixing using the standard light source in 5 mm distance to the specimen.
Setting Time
The setting time of the compositions was determined by measuring the tan δ (delta) value of the mixed base and catalyst paste in dependence on the time at 23° C. and 50% humidity by using a MCR 300 rheometer (plate/plate measurement system, 1 mm gap) from Anton Paar company. The setting time "tE" and the working time "tA" were determined with the software supplied with the instrument using a curve analysis via tangent method. As known to the skilled person in the art, the tan δ value is the quotient of the plastic and elastomeric portion of the composition.

Experiments that required radiation exposure, were conducted by exposing the closed gap of the measuring system from the side in a 5 mm distance starting 75 sec. after start of mix for 10 sec. to light
Shore Hardness
The Shore hardness A was determined according to DIN 53505:2000-8 using a "Härteprüfgerät Zwick 3100/Prüfeinrichtung 7206" (Zwick GmbH & Co. Ulm) as the measuring device. Necessary light exposures of the specimens were done in a Visio™ Beta device applying Program 1 at atmospheric pressure (no vacuum).
Tensile Strength and Elongation at Break
Tensile strength and elongation at break were measured according to DIN 53504:2015-08 form S2. The specimens were measured 24 hours after cure. For determination of the values five independent measurements were performed. A "Universalprüfmaschine Zwick 1435" (Zwick GmbH & Co. Ulm) was used as the measuring device. Necessary light exposures of the specimens were done in a Visio™ Beta device in Program 1 at atmospheric pressure (no vacuum).
Viscosity
The viscosity is a commonly used parameter to characterize the rheological behavior of pasty systems. For the measurement a rheometer with a plate/plate-system (diameter: 20 mm) was used. During the measurement which was accomplished at 23° C. A constant measuring gap was adjusted to 0.2 mm. A viscosity curve of the paste was provided by variation of the shear rate. During the measurement the shear rate was increased from 10 to 100 l/s in steps of 10 l/s. Each measuring point was kept for 5 s. Two independent measurements were performed. A "Physica Rheometer MCR300" (Anton Paar GmbH. Graz) was used as the measuring device.
Measurement of Oxygen Inhibition Layer
The mixed material was filled in a round mold (diameter=20±0.5 mm and height=1.5±0.3 mm) directly set on a glass plate. After filling the mold the specimen was directly put into the Visio™ Beta device in Program 1 at atmospheric pressure (no vacuum) and stored in the dark. After all together 15 min a fluff free cloth with ethanol was used to cleanse the surface of the set material. The weight of the set and cleansed material was subtracted from the weight of the freshly applied material. The loss is measured in mg and then divided with 3.14, the result is given in [mg/cm$^2$].

Materials

The following materials were used:

TABLE 1

| Name | Description |
|---|---|
| APE | Aziridino polyether<br>Chemical curing component<br>Mn: about 6,000 (from EO (ethylene oxide) I THF (tetrahydro furane); obtainable as described in example 20 of U.S. Pat. No. 3,453,242 |
| VISIOMER HEMA TMDI | Diurethanedimethacrylate;<br>CAS: No. 72869-86-4<br>Radiation curing component |
| DESMA | Polyurethane methacrylate;<br>CAS: 1101874-33-2<br>Radiation curing component |
| DDDMA | Dodecandiol-dimethacrylate,<br>CAS: 72829-09-5<br>Radiation curing component |
| TEGDMA | Triethylenglycol-dimethacrylat;<br>CAS: 109-16-0<br>Radiation curing component |
| EO/PO block copolymer | Non-ionic surfactant; CAS: 9003-11-6 |
| Diatomaceous Earth | Filler, CAS: 68855-54-9 |
| Fatty Acid Triglycerides | Fat, CAS: 67701-27-3 |
| Dimethylaminobenzoate | Accelerator; CAS 10287-53-3 |
| Camphorquinone | Initiator; CAS: 10373-78-1 |
| Impregum ™ Soft Catalyst Paste | Chemical curing catalyst paste; 3M, lot# 632421 |
| Lauryl imidazole | Retarder; CAS: 4303-67-7 |
| N,N-Dimethyl alkylamine | Stabilizer; CAS: 68390-97-6 |

General Preparation

Base Paste

In a vessel tri-glyceride and lauryl imidazole were mixed with the aziridino polyether at 90° C. Afterwards the melt was cooled to 23° C. with a cooling drum machine. Finally the filler, pigment, flavor, amine, (meth)acrylates and plasticizer according to Table 2 were added. The whole composition was kneaded.

Catalyst Paste:

Catalyst paste 1 was produced by mixing 100 g of the catalyst paste of commercially available Impregum™ Soft and 2 g of camphorquinone.

Catalyst paste 2 corresponds to the catalyst paste of Impregum™ Soft (without camphorquinone).

Example Preparation

Base pastes and catalyst pastes as shown in Table 2 were prepared.

Base paste and catalyst paste were mixed in a 50 ml cartridge (SulzerMixpac) at a ratio of v/v=4:1.

In a first series of experiments the materials were mixed through a static mixing tip and handled at ambient conditions without being exposed to the light of a curing lamp.

In a second series these measurements were repeated after exposing the freshly mixed material to light.

The compositions were tested for consistency, tensile strength, Shore hardness A and inhibition layer. The results are given in Table 3.

TABLE 2 all amounts are in parts by weight

| | Example | | | | | | |
|---|---|---|---|---|---|---|---|
| Base Paste | 1 | C.E. 2 | 3 | C.E. 4 | 5 | 6 | 7 |
| VISIOMER HEMA TMDI | 34.75 | 34.75 | 34.75 | 34.75 | | | |
| DESMA | | | | | 34.75 | | |
| DDDMA | | | | | | 34.75 | |
| TEGDMA | | | | | | | 34.75 |
| Diatomaceous Earth | 13.40 | 13.40 | 13.40 | 13.40 | 13.40 | 13.40 | 13.40 |
| Dimethylamino-ethylbenzoat | 1.25 | 1.25 | | | 1.25 | 1.25 | 1.25 |
| EO/PO block copolymer | 8.00 | 8.00 | 8.00 | 8.00 | 8.00 | 8.00 | 8.00 |
| Pigment | 0.30 | 0.30 | 0.30 | 0.30 | 0.30 | 0.30 | 0.30 |
| Flavor | 0.30 | 0.30 | 0.30 | 0.30 | 0.30 | 0.30 | 0.30 |
| APE | 76.50 | 76.50 | 76.50 | 76.50 | 76.50 | 76.50 | 76.50 |
| N,N-Dimethyl alkylamine | 0.04 | 0.04 | 0.04 | 0.04 | 0.04 | 0.04 | 0.04 |
| FATTY ACID TRIGLYCERIDES | 8.44 | 8.44 | 8.44 | 8.44 | 8.44 | 8.44 | 8.44 |
| Lauryl imidazole | 1.02 | 1.02 | 1.02 | 1.02 | 1.02 | 1.02 | 1.02 |
| Catalyst Paste | 1 | 2 | 1 | 2 | 1 | 1 | 1 |

TABLE 3

| | | | Example | | | | | | |
|---|---|---|---|---|---|---|---|---|---|
| | | | 1 | C.E. 2 | 3 | C.E. 4 | 5 | 6 | 7 |
| Consistency | with light exposure | [mm] | 20.0 | 42.0 | 34.0 | 42.0 | 18.5 | 40.0 | 39.5 |
| Consistency | no light exposure | [mm] | 41.5 | 41.5 | 41.0 | 41.5 | 40.0 | 47.0 | 46.0 |
| Tensile strength | with light exposure | [MPa] | 7.37 | 1.63 | 6.80 | 1.42 | 5.02 | 5.66 | 6.50 |
| Tensile strength | no light exposure | [MPa] | 1.65 | 1.45 | 1.55 | 1.64 | 1.52 | 1.29 | 1.25 |
| Inhibition layer | with light exposure | [mg/cm$^2$] | 0.0 | 0.0 | 0.0 | −0.9 | 0.0 | 0.0 | 0.0 |
| Shore Hardness A after 24 h | with light exposure | | 75 | 43 | 70 | 45 | 72 | 79 | 76 |
| Shore Hardness A after 24 h | no light exposure | | 45 | 44 | 46 | 46 | 45 | 43 | 42 |

The experiments demonstrate that properties like consistency, tensile strength and Shore hardness can be influenced by exposing the material according to the invention to light.

In particular, it was found that the consistency of the mixed material can be reduced (this means the viscosity is increased) by exposure to light such that a thick material was obtained which had the capability to function as dental retraction material.

Further, after having been thickened by exposure to light, the material cured in a regular way to a final rubber which showed good impression material properties.

In addition, surprisingly no inhibition layer was detected with the compositions described in the present text despite the fact that (meth)acrylates are known to develop such a layer when cured at the presence of oxygen.

Thus, the material as described in the present text can be used together with the commercially available dental impression material Impregum™ Penta™ Soft (3M Oral Care/3M ESPE) as the cured composition did not show a smear layer or oxygen inhibition layer which could prevent a good connection to a typical polyether containing tray impression material.

What is claimed is:

1. A curable composition comprising:
   a Base Part comprising a resin matrix, the resin matrix comprising:
      cationically curable components (A) comprising an aziridino moiety, and
      radiation curable components (B) comprising a (meth)acrylate moiety,
      wherein the cationically curable components (A) and radiation curable components (B) are present in a weight ratio of 10:1 to 1:1; and
   a Catalyst Part comprising a curing system,
      the curing system comprising:
         a starter (A-S), and
         a photo-initiator (B-I),
   wherein the Base Part and the Catalyst Part are separate, the curable composition void of reinforcing fillers and characterized by a Shore hardness A of 50 to 90, as determined according to DIN 53505:2000-8, 24 h after mixing the Base Part and the Catalyst Part and being exposed to light.

2. The curable composition of claim 1, the cationically curable components (A) being characterized by at least one of the following:
   molecular weight: from 150 to 20,000 g/mol; and
   viscosity: from 15 to 300 Pa*s at 23° C.

3. The curable composition of claim 1, the radiation curable components (B) being characterized by at least one of the following:
   molecular weight: from 200 to 3,000 g/mol; and
   viscosity: from 0.01 to 100 Pa*s at 23° C.

4. The curable composition of claim 1, the starter (A-S) selected from a Lewis acid, a Brønsted acid, a precursor of a Lewis acid, a precursor of a Brønsted acid, or a combination thereof.

5. The curable composition of claim 1, the photo-initiator (B-I) being characterized by at least one of the following:
   having a light absorption band in the range of 300 to 800 nm; and
   molecular weight: from 50 to 1,000 g/mol.

6. The curable composition of claim 1, the Base Part further comprising an accelerator.

7. The curable composition of claim 6, wherein the accelerator is present in an amount from 0 to 5 wt. %.

8. The curable composition of claim 1, further comprising at least one of the following component(s):
   non-reinforcing filler(s);
   surfactant(s); and
   additive(s) selected from pigment(s), stabilizer(s), plasticisers, liquids, diluting agents, triacyl esters of glycerol, astringents(s), retarder(s), and mixtures thereof,
   wherein the filler(s), surfactant(s), and additive(s) are each independently present in the Base Part or Catalyst Part.

9. The curable composition of claim 8, wherein:
   non-reinforcing filler(s) is present in an amount from 0 to 60 wt. %, and
   additive(s) is present in an amount from 0 to 50 wt. %.

10. The curable composition of claim 1, wherein:
   cationically curable components are present in an amount from 5 to 90 wt. %,
   radiation curable components are present in an amount from 1 to 30 wt. %,
   starter is present in an amount from 2 to 20 wt. %, and
   photo-initiator is present in an amount from 0.01 to 3 wt. %,
   wt. % with respect to the weight of the whole composition.

11. The curable composition of claim 1, being characterized by one or more of the following:
   viscosity of Base Part and/or Catalyst Part: from 2 to 500 Pa*s at 23° C.;
   consistency: less than 40 mm, after exposure to light and if determined according to ISO 4823:2015-08:2007-10; and
   hardening within 15 min within a temperature range from 20 to 40° C. to a rubber elastic mass after mixing the Base Part and the Catalyst Part.

12. The curable composition of claim 1, further comprising one or more of:
   filler(s),
   surfactant(s), and
   accelerator,
   wherein:
      the starter (A-S) is selected from Lewis acids, Brønsted acids, precursors of Lewis acids, precursors of Brønsted acids, or a mixture thereof, and
      the photo-initiator (B-I) is selected from alpha-diketone and phosphine oxide components.

13. A cured composition obtained by mixing and subsequently radiating the Base Part and the Catalyst Part of claim 1, the cured composition being characterized by one or more of the following features:
   Shore hardness A: from 40 to 90 as determined according to DIN 53505:2000-8, 24 h after the mixing and radiating;
   Tensile strength: above 4 MPa as determined according to DIN 53504:2015-08, 24 h after the mixing and radiating; and
   being rubber elastic.

14. The curable composition of claim 1, the radiation curable components (B) further comprising a urethane moiety.

15. The curable composition of claim 1, the photo-initiator (B-I) selected from alpha-diketone component(s), phosphine oxide component(s), or a mixtures thereof.

16. A process for preparing a dental impression including sub-gingival parts, the process comprising:
   combining the Base Part and the Catalyst Part of claim 1 to obtain a mixture,
   radiating the mixture to obtain a radiated mixture,
   applying a first portion of the radiated mixture into a tooth sulcus,
   optionally radiating the radiated mixture applied to the tooth sulcus,
   applying a second portion of the radiated mixture to a dental tissue surface, and
   removing the first and second portions of the radiated mixture from the tooth sulcus and the dental tissue surface.

17. The process of claim 16, wherein one or more of:
   the starter
      selected from Lewis acids, Brønsted acids, precursors of Lewis acids, precursors of Brønsted acids, or a mixture thereof;
   the photo-initiator (B-I) selected from alpha-diketone component(s), phosphine oxide component(s), or a mixture thereof,
   the photo initiator being characterized by one or more of the following features:
      having a light absorption band in the range of 300 to 800 nm; and
      molecular weight: from 50 to 1,000 g/mol;
   the cationically curable components (A) being characterized by at least one of the following:
      molecular weight: from 150 to 20,000 g/mol; and
      viscosity: from 15 to 300 Pa*s at 23° C.; and
   the radiation curable components (B) optionally further comprising a urethane moiety, and being characterized by at least one of the following:
      molecular weight: from 200 to 3,000 g/mol; and
      viscosity: from 0.01 to 100 Pa*s at 23° C.

18. A kit of parts comprising:
   the curable composition of claim 1, and
   one or more of:
      an application device;
      a radiation source; and
      a dental impression composition,
      wherein the dental impression composition is different from the curable composition.

19. A process for preparing a dental impression including sub-gingival parts, the process comprising:
   combining the Base Part and the Catalyst Part of claim 1 to obtain a mixture,
   radiating the mixture to obtain a radiated mixture,
   applying the radiated mixture into a tooth sulcus,
   optionally radiating the radiated mixture applied to the tooth sulcus,
   applying a dental impression material to a dental tissue surface, and
   removing the radiated mixture and the dental impression material from the tooth sulcus and the dental tissue surface.

* * * * *